(12) United States Patent
Barber et al.

(10) Patent No.: US 10,502,700 B2
(45) Date of Patent: Dec. 10, 2019

(54) METHODS FOR ANALYZING RESPIRABLE PARTICLES IN BULK MATERIALS

(71) Applicant: United States Gypsum Company, Chicago, IL (US)

(72) Inventors: James W. Barber, Chicago, IL (US); Feng Peng, Libertyville, IL (US)

(73) Assignee: United States Gypsum Company, Chicago, IL (US)

( * ) Notice: Subject to any disclaimer, the term of this patent is extended or adjusted under 35 U.S.C. 154(b) by 76 days.

(21) Appl. No.: 15/642,533

(22) Filed: Jul. 6, 2017

(65) Prior Publication Data

US 2018/0017510 A1    Jan. 18, 2018

Related U.S. Application Data

(60) Provisional application No. 62/361,273, filed on Jul. 12, 2016.

(51) Int. Cl.
*G01N 23/2206* (2018.01)
*G01N 1/40* (2006.01)
(Continued)

(52) U.S. Cl.
CPC ....... *G01N 23/2206* (2013.01); *G01N 1/4005* (2013.01); *G01N 15/1456* (2013.01); *G01N 15/1468* (2013.01); *G01N 23/20091* (2013.01); *G01N 23/2251* (2013.01); *G01N 15/0625* (2013.01); *G01N 23/2005* (2013.01); *G01N 2015/0061* (2013.01); *G01N 2015/1497* (2013.01)

(58) Field of Classification Search
CPC .......... G01N 23/2206; G01N 23/2209; G01N 23/2251; G01N 1/4005; G01N 15/1456; G01N 15/1468
See application file for complete search history.

(56) References Cited

U.S. PATENT DOCUMENTS 9,067,824 B1 * 6/2015 Hansen ..................... C04B 7/12
2001/0053741 A1 * 12/2001 Micco ................... C01B 39/023
502/79

(Continued)

FOREIGN PATENT DOCUMENTS

DE    102013217157 A1    3/2015

OTHER PUBLICATIONS

Draft IMA-Europe standard accepted for CEN PQ procedure, Size Weighted Respirable Fraction—SweRF and Size Weighted Respirable Fraction of Crystalline Silica—SWeRFcs, CEN/TC, Mar. 2010.

(Continued)

*Primary Examiner* — Bryan Bui
(74) *Attorney, Agent, or Firm* — Greer, Burns & Crain, Ltd.; Pradip Sahu; Philip T. Petti

(57) ABSTRACT

Provided is a method for detecting respirable participles in a bulk material comprising particles. The method comprises: analyzing morphology of the particles; analyzing chemical composition of the particles; creating a profile of the particles, wherein each particle in the profile is characterized by its shape, size and chemical composition; selecting particles from the profile which match the size and chemical composition of a respirable particle; and calculating a percentage of the respirable particles in the bulk material.

7 Claims, 25 Drawing Sheets

(51) Int. Cl.
*G01N 23/20091* (2018.01)
*G01N 23/2251* (2018.01)
*G01N 15/14* (2006.01)
*G01N 23/2005* (2018.01)
*G01N 15/00* (2006.01)
*G01N 15/06* (2006.01)

(56) References Cited

U.S. PATENT DOCUMENTS

2013/0280663 A1* 10/2013 Cerecedabalic ....... G01N 25/26
 431/13
2015/0219547 A1 8/2015 Takakura

OTHER PUBLICATIONS

Huffman et al., CCSEM investigation of respirable quartz in air samples collected during power plant maintenance activities, Fuel, vol. 95, Nov. 28, 2011, pp. 365-370.
Le Bond et al., Production of potentially hazardous respirable silica airborne particulate from the burning of sugarcane, Atmospheric Environment, vol. 42, No. 22, Jul. 1, 2008, pp. 5558-2310.
Horwell et al., Characterization of respirable volcanic ash from the Soufriere Hills volcano, Montserrat, with implications for human health hazards, Bulletin of Volcanology; Official Journal of the International Association of Volcanology and Chemistry of the Earth's Interior (IAVCEI), vol. 65, No. 5, Jan. 31, 2003, pp. 346-362.

* cited by examiner

DuPont Richmond RM 80332  Date: 11/21/2011  Sample  Cryst. Silica cont.  0.1

Sample identification FGD Gypsum  Density = 2320 kg/m³  CS Density = 2650
perlite specific gravity 2.32  SWeRF = 1.6 %  SWeRFcs = 0.001
                                              RJ Lee Total Crystalline Silica  0.1
                                              RJ Lee Respirable Silica < 10μ  < 0.01
                                              RJ Lee Respirable Silica < 5μ   < 0.01

FIG. 2B

Dayton Power Light RM 80570  Date: 7/2/1997  Sample  Cryst. Silica cont.  0.2

Sample identification FGD Gypsum  
perlite specific gravity 2.3

Density = 2300 kg/m³  
SWeRF = 0.0 %

CS Density = 2650  
SWeRFcs = 0.0  
RJ Lee Total Crystalline Silica  0.2  
RJ Lee Respirable Silica < 10µ  < 0.05

FIG. 3B

RM 100125 Gypsum  Date: 5/14/2015  Sample  Cryst. Silica cont.  3.6

Sample identification recycle wallboard
perlite specific gravity 2.32

Density = 2320 kg/m³  CS Density = 2650
SWeRF = 0.80 %  SWeRFcs = 0.03
  RJ Lee Total Crystalline Silica  3.6
  RJ Lee Respirable Silica < 10µ  1.31

FIG. 4B

METHODS FOR ANALYZING RESPIRABLE PARTICLES IN BULK MATERIALS

CROSS-REFERENCE TO RELATED APPLICATIONS

This application claims the benefit of priority from U.S. Provisional Patent Application 62/361,273 filed on Jul. 12, 2016, the entire disclosure of which is incorporated herein by reference.

TECHNICAL FIELD

This invention provides methods for accurate and rapid detection of respirable particles in bulk materials.

BACKGROUND

Many compounds used by the building construction industry are bulk materials, including, but not limited to, gypsum, calcined gypsum, mica, cement, calcium carbonate and sand. These dry compounds comprise a population of particles of different sizes.

Particles which are smaller than 20 microns are referred to respirable particles because these particles can be dispersed into the air. These particles can be then inhaled by workers, which should be avoided. Thus, there is a need to analyze a powder sample and provide an accurate estimate whether the sample comprises respirable particles and the percentage of such particles in the sample.

The standard procedure for respirable silica requires the sample in analysis to be treated with acid to eliminate most of the sample matrix. The remaining material is examined for crystalline silica. The weight of crystalline silica is determined using X-ray Diffraction or FTIR. This number is reported as Total Crystalline Silica. The second step requires the sample to be dispersed in alcohol and transferred to a silver membrane and the mass of crystalline silica determined for the <10μ fraction. A determination is also provided for the <5μ fraction.

The criteria in the Globally Harmonized System (GHS) have the fine fraction of silica classified as specific target organ toxicity in this case, the lung. Generic cut-off values for products containing a fine fraction of crystalline silica trigger a need for a method for the quantification of the fine fraction of crystalline silica in bulk materials.

The European Union has promoted an analysis for silica in bulk materials which culminated in the publication of a new standard for measuring the amounts of respirable particles in bulk materials. The standard has two parts:

1. Determination of Size-Weighted Potential Respirable Fraction (SWeRF); and
2. Size-Weighted Potential Respirable Fraction of Crystalline Silica (SWeRF$_{CS}$)

The method is to be used for comparing the potential health risks of bulk materials. The method does not predict how a material will disperse in air, but quantifies the respirable fraction. The particles that present a larger health risk are weighed more in the calculation. The advantage of the method is it provides an unambiguous characterization of the bulk material. The term "potential" is used to indicate that the standard does not analyze airborne particles.

The standard describes a method using sedimentation and a calculation method based on particle size distribution (PSD). The calculation can only be used after the results are validated using the sedimentation data. The calculation method requires that the particles have the same density or in the case of mixture with different materials that they have the same PSD. A plot is made to compare the sedimentation PSD with the Stokes' Law and the convention described in CSN EN 481 (European Standards EN 481 "Workplace atmospheres—size fraction definitions for measurement of airborne particles"). However, in this calculation method, the dynamic form factor is neglected where in the sedimentation method, the dynamic form factor is assumed to be equal in air and liquid. Thus, there remains a need for accurate and rapid detection of respirable particles in a bulk material.

SUMMARY

At least some of these needs are addressed by the present methods which are based on analyzing particles for their morphology and chemical composition and creating a profile for a sample in which each particle is characterized by its morphology and chemical composition.

This invention provides a method for detecting respirable participles in a bulk material comprising particles. The method comprises:
- analyzing morphology of the particles;
- analyzing chemical composition of the particles;
- creating a profile of the particles, wherein each particle in the profile is characterized by its shape, size and chemical composition;
- selecting particles from the profile which match the size and chemical composition of a respirable particle; and
- calculating a percentage of the respirable particles in the bulk material.

In this method, the morphology and chemical composition of the particles can be analyzed by a computer-controlled scanning electron microscope interfaced with an energy dispersive X-ray spectrometer (SEM☐EDS). The method may comprise a step of resuspending the particles of the bulk material, such as gypsum or calcium carbonate, in a medium (water or organic solvent), and filtering the suspension through a filter with a nominal pore size sufficiently small to retain the particles in the respirable size range. In the method, the particles can be retained on a filter. The morphology and chemical composition of the particles are analyzed by an automated SEM☐EDS. Various bulk materials can be analyzed, including mixtures of inorganic compounds.

The present method can be used to analyze respirable particles, such as for example silica ($SiO_2$), smaller than 20 microns. The present method can be also used to analyze respirable particles, such as for example silica ($SiO_2$), smaller than 10 microns.

BRIEF DESCRIPTION OF THE DRAWINGS

FIG. 2B are calculations in connection with the plot of FIG. 2A.

FIG. 3B are calculations in connection with the plot of FIG. 3A.

FIG. 4B are calculations in connection with the plot of FIG. 4A.

DETAILED DESCRIPTION

Figure 1:
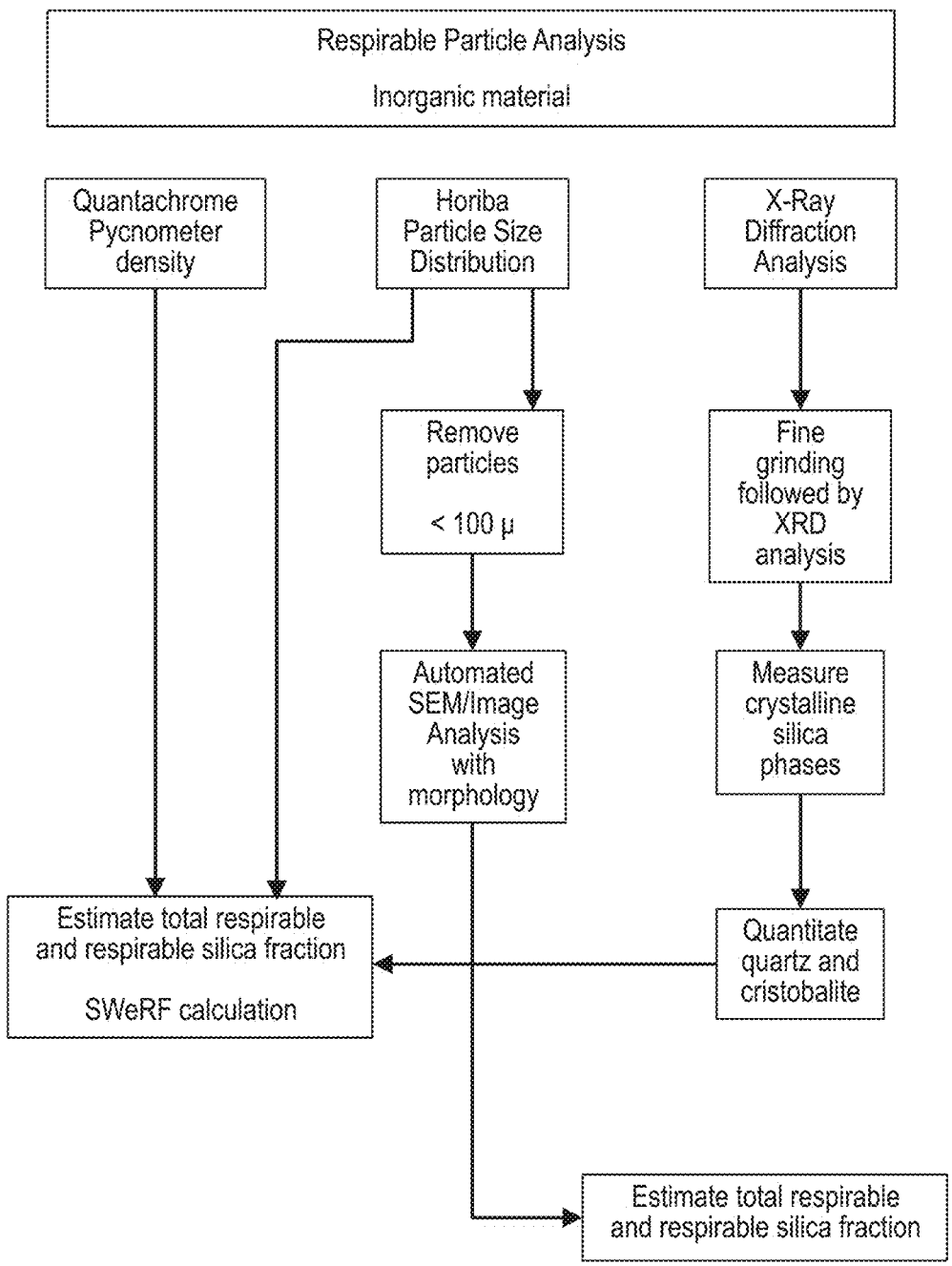
FIG. 1 is a diagram of methods for respirable particle analysis.

Provided is a method for examining the respirable fraction in bulk materials. The method comprises the following two steps. In step one, a sample is analyzed for particle size distribution and density. This step determines the total proportion of respirable particles in the sample. In step two, the amount of crystalline silica (also known as silicon dioxide or quartz) in the sample is determined. Various matrices can be analyzed by this method, including gypsum, cement, mica, calcium carbonate, sand, etc. The method is illustrated in FIG. 1 in comparison to other methods.

Step one can be performed by using a Quantachrome Pycnometer for a density measurement, followed by an analysis with a particle size analyzer (such as for example, Horiba LA-950V2) and the SWeRF equation which is validated for individual matrices. In step two, the mass of silica in the respirable fraction can be estimated by using a scanning electron microscope which eliminates the need for X-Ray Diffraction Instrument. In further embodiments, a scanning electron microscope interfaced with an energy dispersive X-ray spectrometer can be used to analyze particles for their morphology, including shape and size, and also a chemical (elemental composition) of the particles. See FIG. 1 in which the present method is compared to other methods.

In the present method, a scanning electron microscope is used for crystalline identification and morphology. This analysis can be conducted with computer software which captures data for each particle individually, including the particle's shape, size and chemical composition.

Figure 2A:
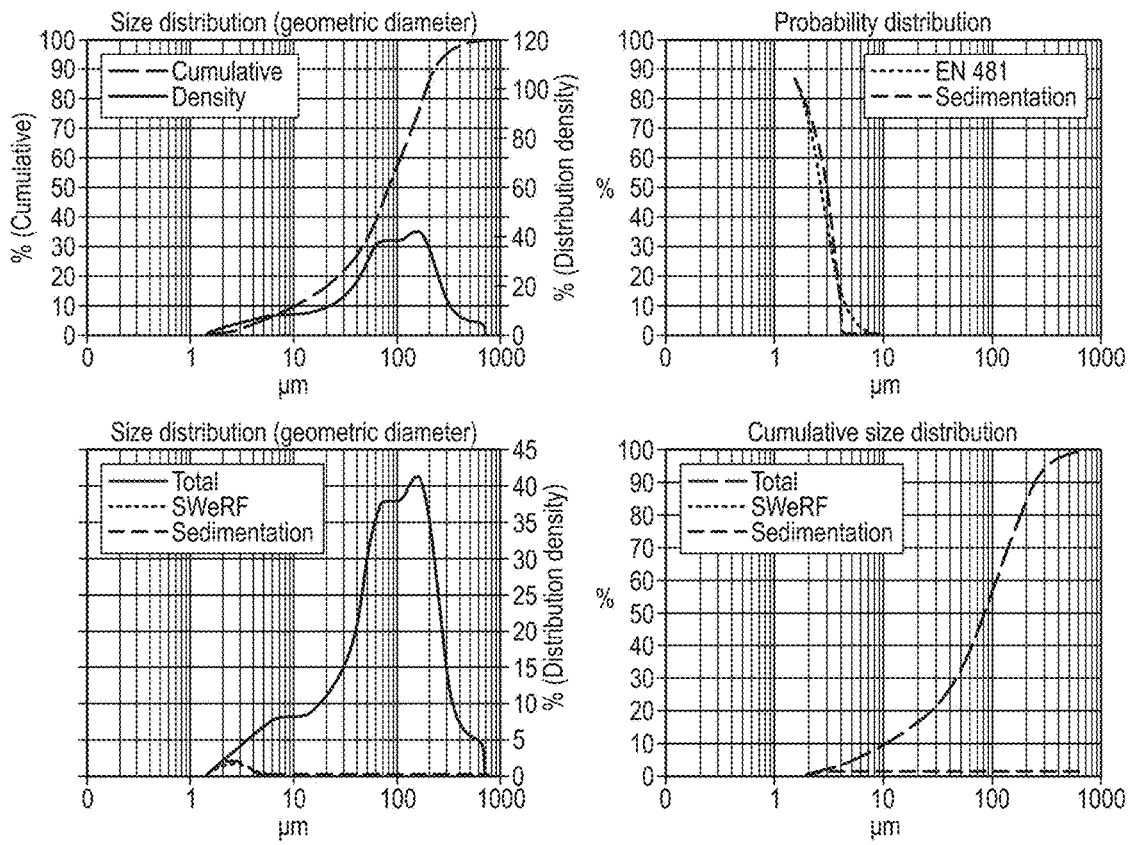
FIG. 2A is a plot for a bulk material comprising a small respirable faction.

In one embodiment of the method, the SWeRF equations are evaluated using the CIC particle size analysis and RJ Lee Total Crystalline Silica. A typical graphic output for plotting the PSD for the SWeRF calculation is shown in FIG. 2A. The plot indicates the DuPont Richmond FGD (trimodal PSD) has a small respirable fraction (1.6%). Using the SWeRF and SWeRF$_{CS}$ equations as shown in the Table of FIG. 2B, the RJ Lee and SWeRF$_{CS}$ estimate are in agreement and report 0.01% respirable silica.

Figure 3A:
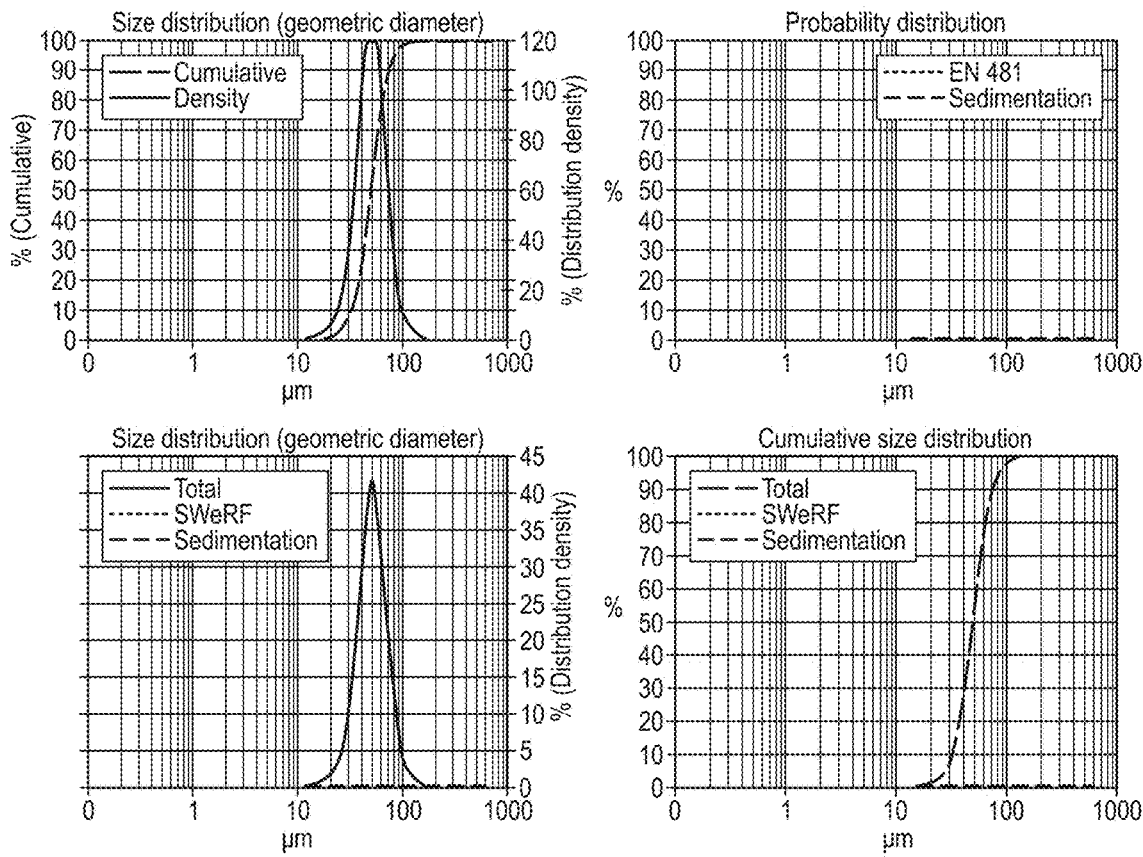
FIG. 3A is a plot for bulk material which does not comprise detectable respirable silica.

As shown in FIG. 3A and the Table of FIG. 3B, the Dayton Power Light FGD illustrates a scenario where the PSD and SWeRF equations indicate no respirable fraction (monomodal PSD) and therefore no respirable silica. The RJ Lee data is indicating total crystalline silica of 0.2% and <10µ respirable silica of 0.2%.

Figure 4A:
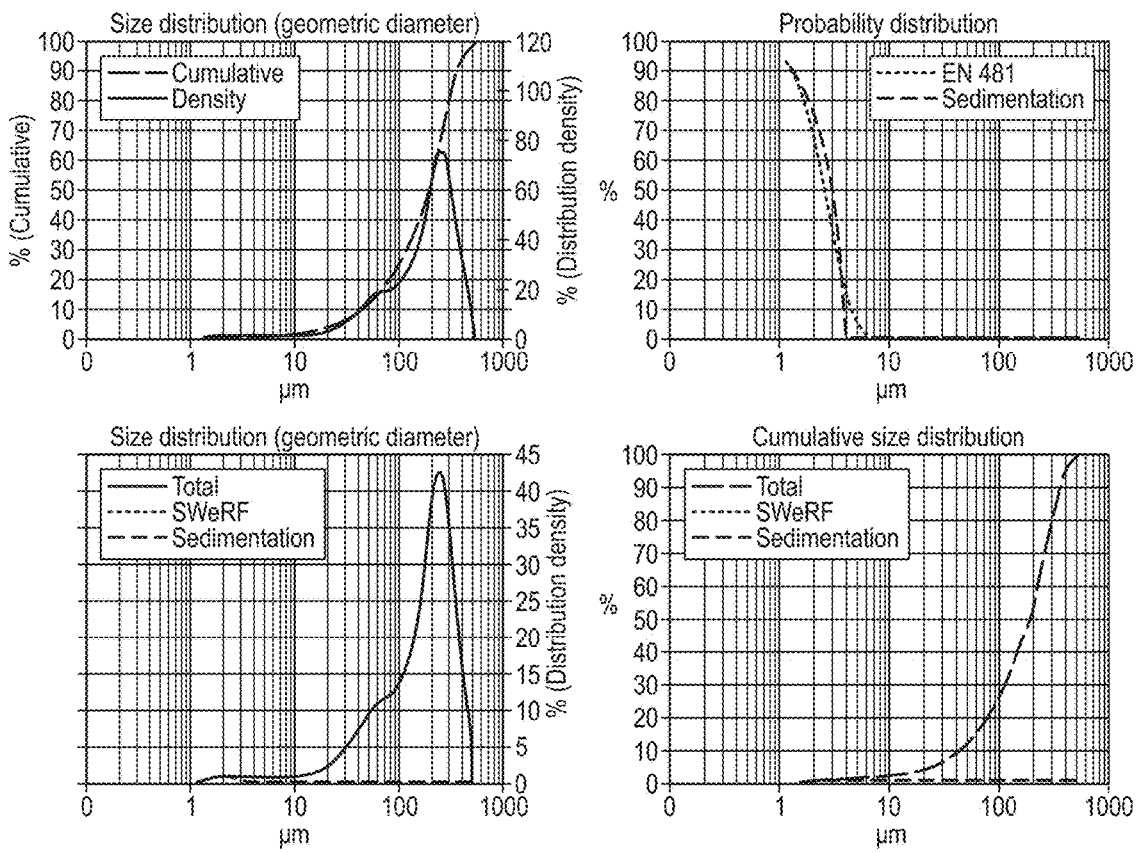
FIG. 4A is a plot of a bulk material comprising a respirable fraction.

As shown in FIG. 4A and the Table of FIG. 4B, the Montreal Recycle material illustrates a scenario where the PSD (bimodal) and SWeRF equations indicate a small respirable fraction in contrast to the RJ Lee data indicating a respirable silica fraction of 1.3%. This is significantly higher than the 0.8% SWeRF estimate. This could require the sedimentation verification for SWeRF.

Table 1 is a summary of several different types of raw materials and how the SWeRF estimates correlate with the RJ Lee respirable silica.

As shown in Table 1, in some examples (Dayton Power FGD, Rodemacher Fly Ash) there are two outputs. This occurs when the SDS gives a range for the density. For example, the Rodemacher SDS provided a density range of 2200-2800 kg/m$^3$. The calculation for SWeRF was performed twice (2200 and 2800 kg/m$^3$).

TABLE 1

| Sample name Haydite RM 81002 | Date: | Sep. 4, 2009 | Sample | | | Cryst. Silica cont. | 33.9 | % |
| Sample identification | | | Density = | 623 | kg/m3 | CS Density = | 2650 | kg/m3 |
| raw material (silica 50-60%) | | | SWeRF = | 46.2 | % | SWeRFcs = | 9.2 | % |
| | | | | | | RJ Lee Total Crystalline Silica | 33.9 | |
| | | | | | | RJ Lee Respirable Silica <10 µ | 8.2 | |
| | | | | | | RJ Lee Respirable Silica <5 µ | 3.4 | |
| Sample Lansing Fly ash RM81141 | Date: | Aug. 20, 2010 | Sample | | | Cryst. Silica cont. | 9.5 | % |
| Sample identification | | | Density = | 2000.0 | kg/m3 | CS Density = | 2650.0 | kg/m3 |
| flyash density 2-3.2 | | | SWeRF = | 25.4 | % | SWeRFcs = | 2.2 | % |
| Sample Lansing Fly ash RM81141 | Date: | Aug. 20, 2010 | Sample | | | Cryst. Silica cont. | 9.5 | % |
| Sample identification | | | Density = | 3200.0 | kg/m3 | CS Density = | 2650.0 | kg/m3 |
| flyash density 2-3.2 | | | SWeRF = | 20.9 | % | SWeRFcs = | 2.2 | % |
| | | | | | | RJ Lee Total Crystalline Silica | 9.5 | |
| | | | | | | RJ Lee Respirable Silica <10 µ | 2.6 | |
| | | | | | | RJ Lee Respirable Silica <5 µ | 1.2 | |
| Sample slate RM80062 | Date: | | Sample | | | Cryst. Silica cont. | 16.4 | % |
| Sample identification | | | Density = | 1500 | kg/m3 | CS Density = | 2650 | kg/m3 |
| slate density 1.47-1.53 | | | SWeRF = | 5.8 | % | SWeRFcs = | 0.7 | % |
| | | | | | | RJ Lee Total Crystalline Silica | 16.4 | |
| | | | | | | RJ Lee Respirable Silica <10 µ | 0.2 | |
| | | | | | | RJ Lee Respirable Silica <5 µ | N/A | |

TABLE 1-continued

| Sample | Date | | | | | | |
|---|---|---|---|---|---|---|---|
| Sample mica RM79833 Sample identification slate density 1.80 | Date: | Sample Density = SWeRF = | 1800 7.8 | kg/m3 % | Cryst. Silica cont. CS Density = SWeRFcs = RJ Lee Total Crystalline Silica RJ Lee Respirable Silica <10 μ RJ Lee Respirable Silica <5 μ | 2.3 2650 0.1 2.3 0.3 0.2 | % kg/m3 % |
| Sample Termolita perlite (Microsil-200) RM81137 Sample identification perlite specific gravity | Date: Aug. 18, 2010 | Sample Density = SWeRF = | 2350 2.4 | kg/m3 % | Cryst. Silica cont. CS Density = SWeRFcs = RJ Lee Total Crystalline Silica RJ Lee Respirable Silica <10 μ RJ Lee Respirable Silica <5 μ | 0.10 2650 0.002 <0.1 <0.01 N/A | % kg/m3 % |
| Sample Microsill 200S RM81249 Sample identification perlite specific gravity 2.35 | Date: Jun. 14, 2011 | Sample Density = SWeRF = | 2350 0.8 | kg/m3 % | Cryst. Silica cont. CS Density = SWeRFcs = RJ Lee Total Crystalline Silica RJ Lee Respirable Silica <10 μ RJ Lee Respirable Silica <5 μ | 0.3 2650 0.002 0.3 0.01 N/A | % kg/m3 % |
| DuPont Richmond RM80332 Sample identification FGD Gypsum perlite specific gravity 2.32 | Date: Nov. 21, 2011 | Sample Density = SWeRF = | 2320 1.6 | kg/m3 % | Cryst. Silica cont. CS Density = SWeRFcs = RJ Lee Total Crystalline Silica RJ Lee Respirable Silica <10 μ RJ Lee Respirable Silica <5 μ | 0.1 2650 0.001 0.1 <0.01 <0.01 | % kg/m3 % |
| DuPont Richmond RM80332 Sample identification FGD Gypsum perlite specific gravity 2.32 | Date: Nov. 21, 2011 | Sample Density = SWeRF = | 2960 1.182038043 | kg/m3 % | Cryst. Silica cont. CS Density = SWeRFcs = RJ Lee Total Crystalline Silica RJ Lee Respirable Silica <10 μ RJ Lee Respirable Silica <5 μ | 0.1 2650 0.001 0.1 <0.01 <0.01 | % kg/m3 % |
| Dayton Power Light RM80570 Sample identification FGD Gypsum perlite specific gravity 2.3 | Date: Jul. 2, 1997 | Sample Density = SWeRF = | 2300 0.0 | kg/m3 % | Cryst. Silica cont. CS Density = SWeRFcs = RJ Lee Total Crystalline Silica RJ Lee Respirable Silica <10 μ | 0.2 2650 0.0 0.2 <0.05 | |
| Dayton Power Light RM80570 Sample identification FGD Gypsum perlite specific gravity 2.3 | Date: Jul. 2, 1997 | Sample Density = SWeRF = | 2500 0.0 | kg/m3 % | Cryst. Silica cont. CS Density = SWeRFcs = RJ Lee Total Crystalline Silica RJ Lee Respirable Silica <10 μ | 0.2 2650 0.0 0.2 <0.05 | |
| Nepheline Syenite RM62074 Sample identification perlite specific gravity 2.3 | Date: Jul. 2, 1997 | Sample Density = SWeRF = | 2610 44.6 | kg/m3 % | Cryst. Silica cont. CS Density = SWeRFcs = RJ Lee Total Crystalline Silica RJ Lee Respirable Silica <10 μ | 0.1 2650 0.0 0.1 <0.1 | |
| 2015-134 Rodemacher fly ash C Sample identification fly ash specific gravity 2.2 | Date: Apr. 24, 2015 | Sample Density = SWeRF = | 2200 10.8 | kg/m3 % | Cryst. Silica cont. CS Density = SWeRFcs = RJ Lee Total Crystalline Silica RJ Lee Respirable Silica <10 μ | 2 2650 0.19 2 0.13 | |
| 2015-134 Rodemacher fly ash C Sample identification fly ash specific gravity 2.8 | Date: Apr. 24, 2015 | Sample Density = SWeRF = | 2800 9.3 | kg/m3 % | Cryst. Silica cont. CS Density = SWeRFcs = RJ Lee Total Crystalline Silica RJ Lee Respirable Silica <10 μ | 2 2650 0.19 2 0.13 | |
| 2015-137 Termolito perlite #1 Sample identification perlite specific gravity 2.35 | Date: Apr. 27, 2015 | Sample Density = SWeRF = | 2350 0.8 | kg/m3 % | Cryst. Silica cont. CS Density = SWeRFcs = RJ Lee Total Crystalline Silica RJ Lee Respirable Silica <10 μ | 1.5 2650 0.01 1.5 0.19 | |
| 2015-137 Termolito perlite #2 Sample identification perlite specific gravity 2.35 | Date: Apr. 27, 2015 | Sample Density = SWeRF = | 2350 0.8 | kg/m3 % | Cryst. Silica cont. CS Density = SWeRFcs = RJ Lee Total Crystalline Silica RJ Lee Respirable Silica <10 μ | 1.9 2650 0.01 1.9 0.3 | |
| RM 100125 Gypsum Sample identification recycle wallboard specific gravity 2.32 | Date: May 14, 2015 | Sample Density = SWeRF = | 2320 0.80 | kg/m3 % | Cryst. Silica cont. CS Density = SWeRFcs = RJ Lee Total Crystalline Silica RJ Lee Respirable Silica <10 μ | 3.6 2650 0.03 3.6 1.31 | |

Figure 5:
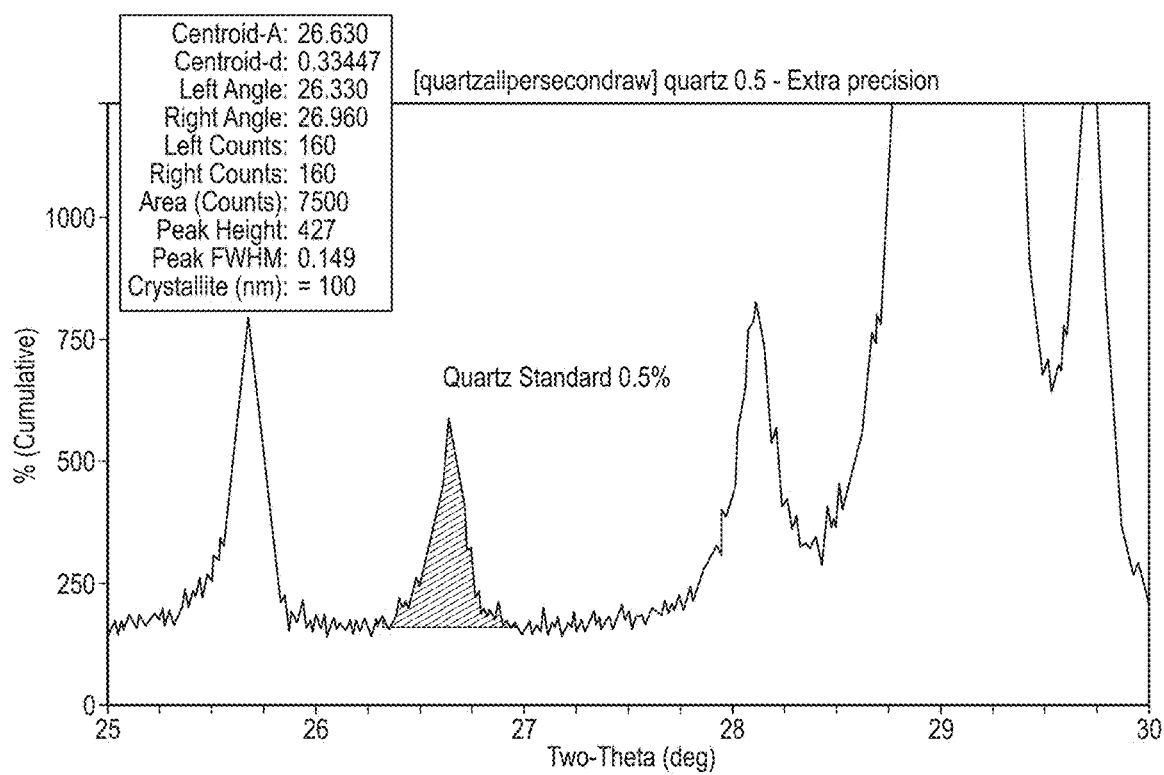
FIG. 5 is a scan of gypsum spiked with 0.5% of quartz.
Figure 6:
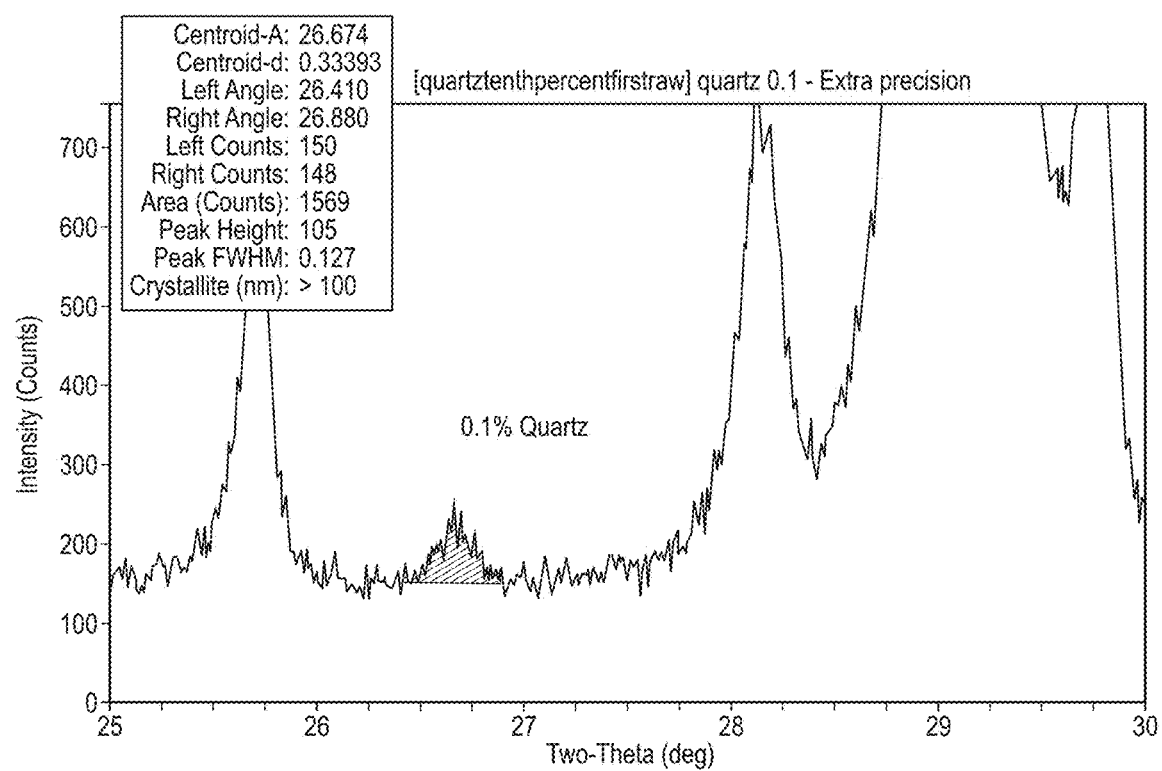
FIG. 6 is a scan of gypsum spiked with 0.1% of quartz.
Figure 7:
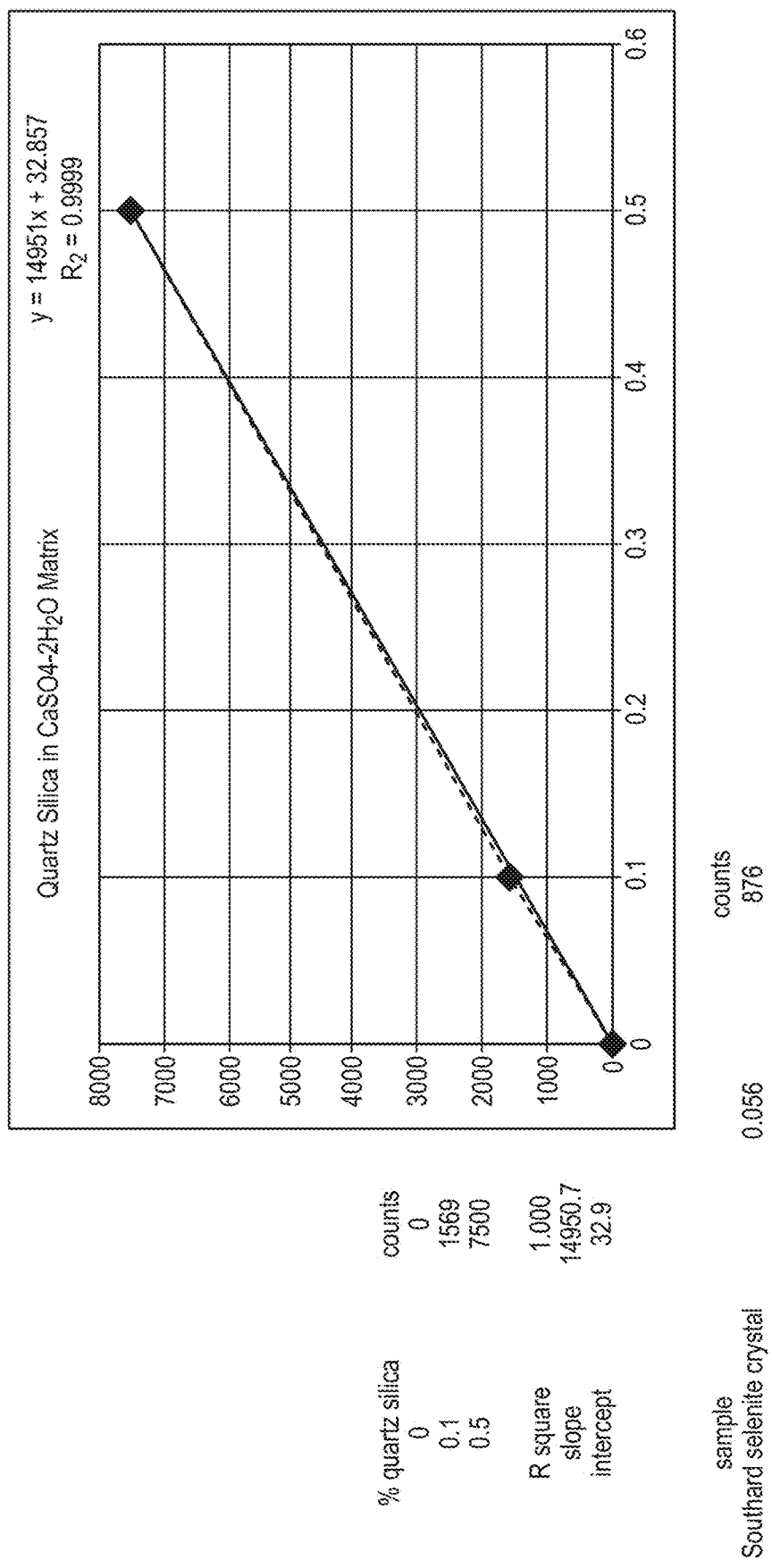
FIG. 7 is a plot with three calibration points.
Figure 8:
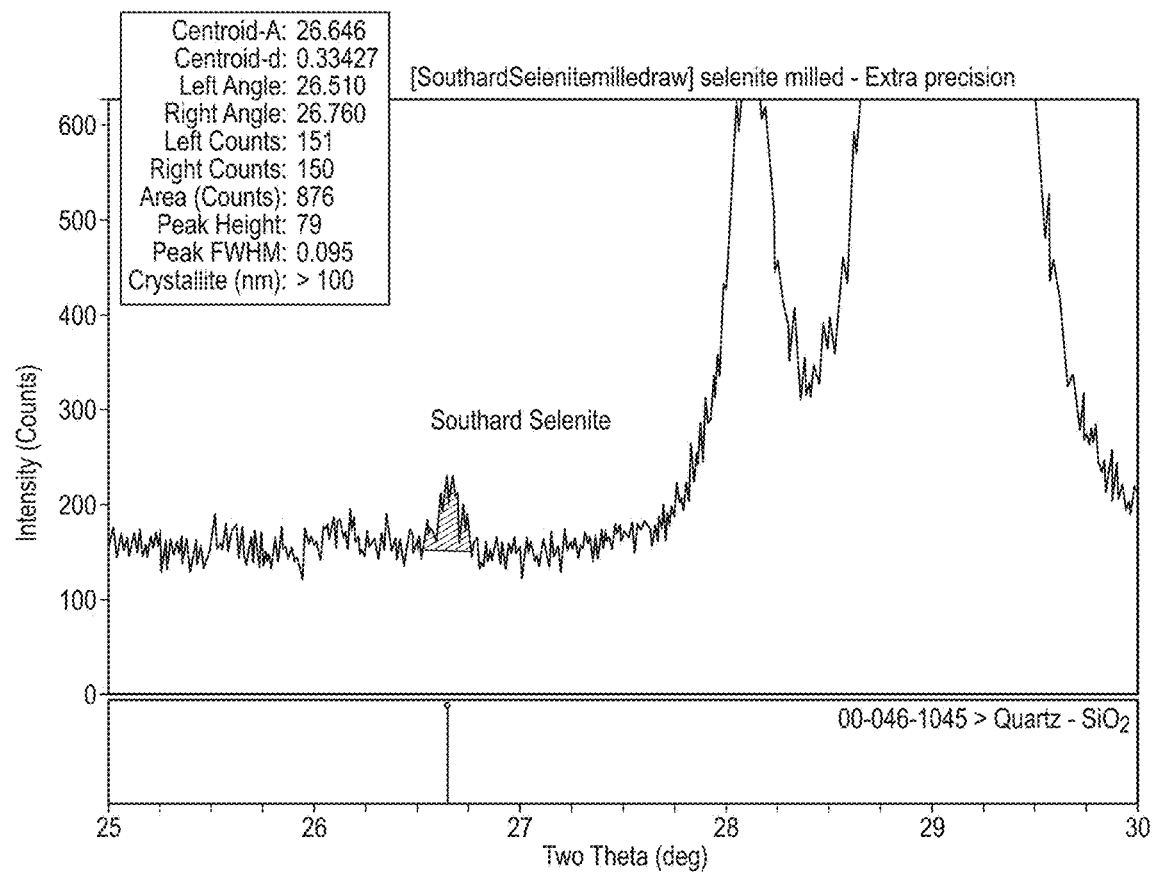
FIG. 8 is a scan of selenite comprising quartz.
Figure 9:
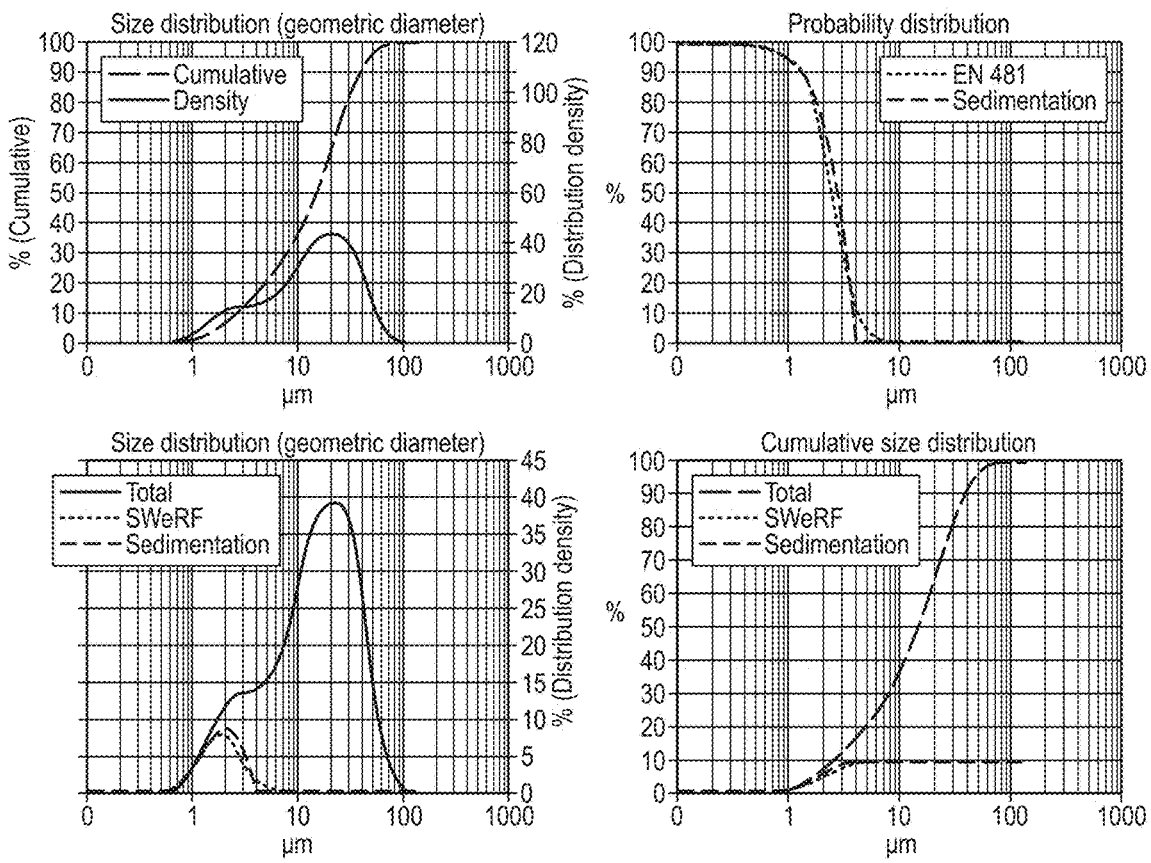
FIG. 9 is a first plot of filler Microwhite 100.
Figure 10:
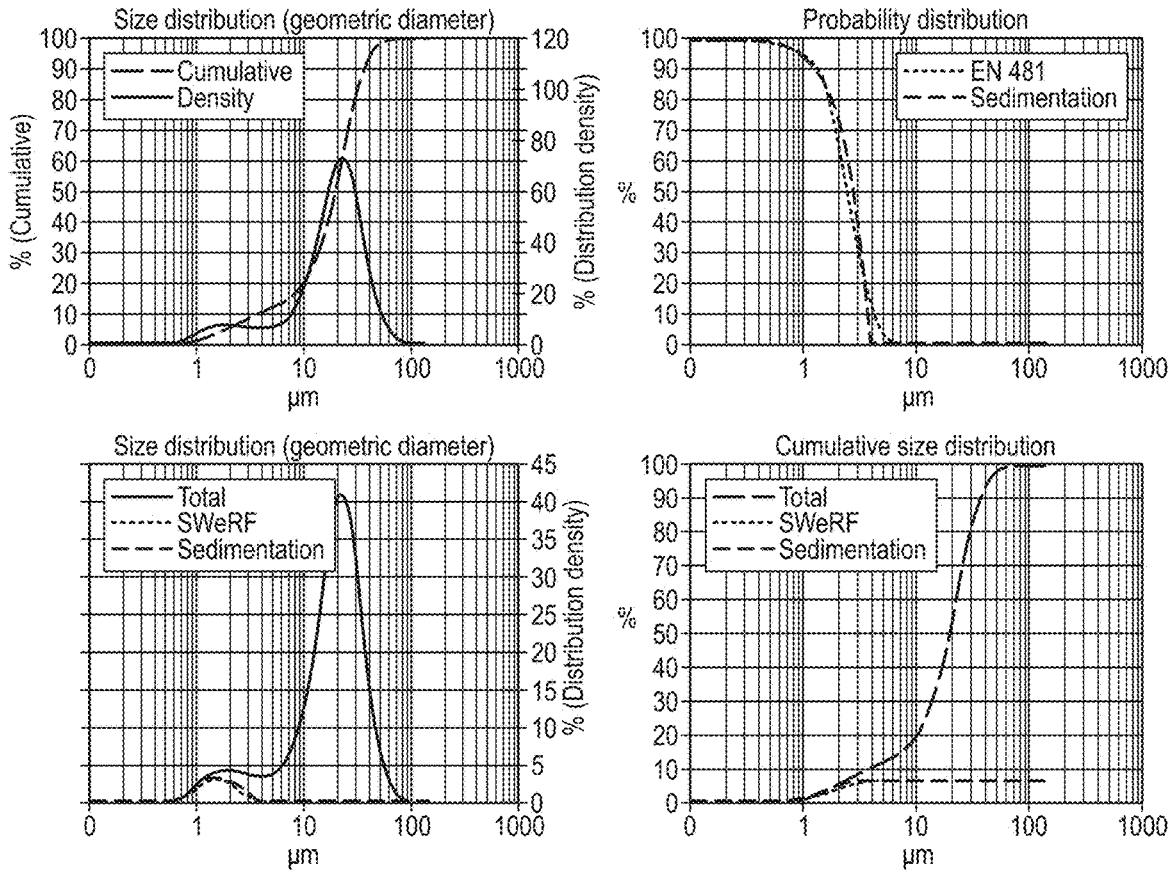
FIG. 10 is a first plot of filler Pulpro-20.
Figure 11:
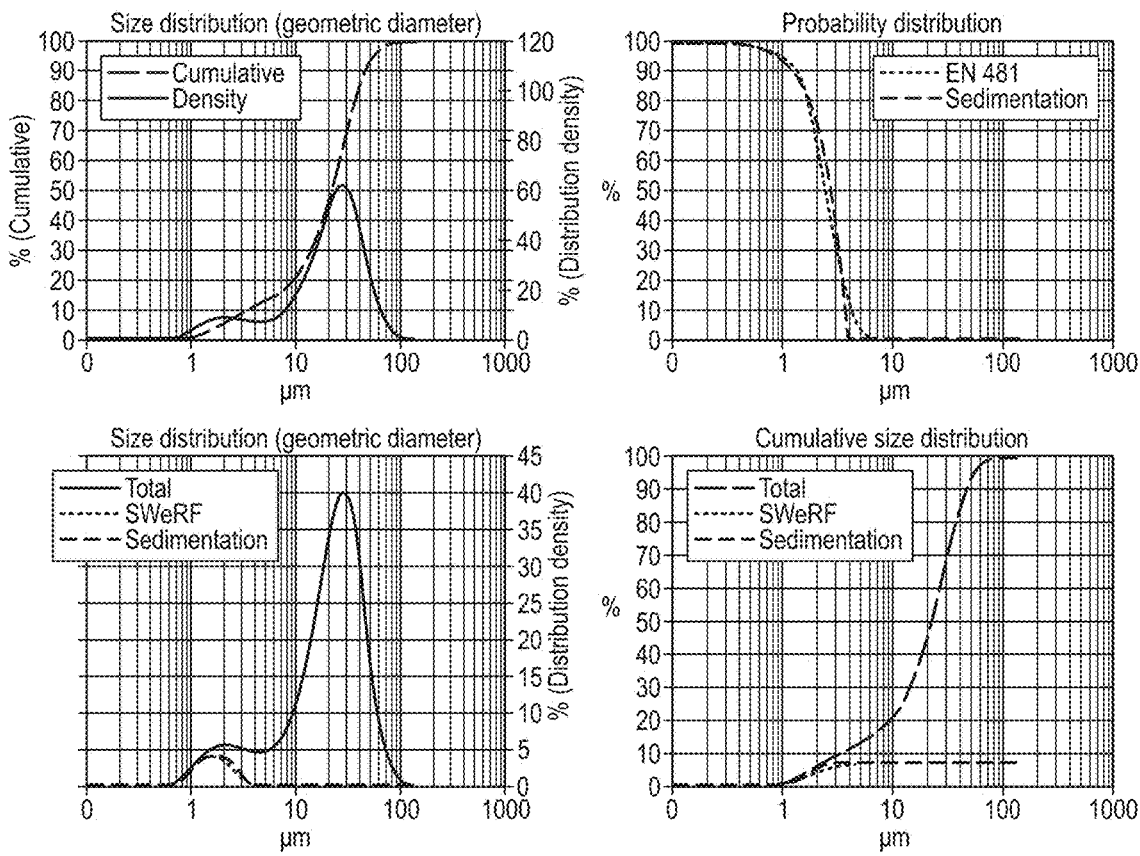
FIG. 11 is a pot of filler #3.
Figure 12:
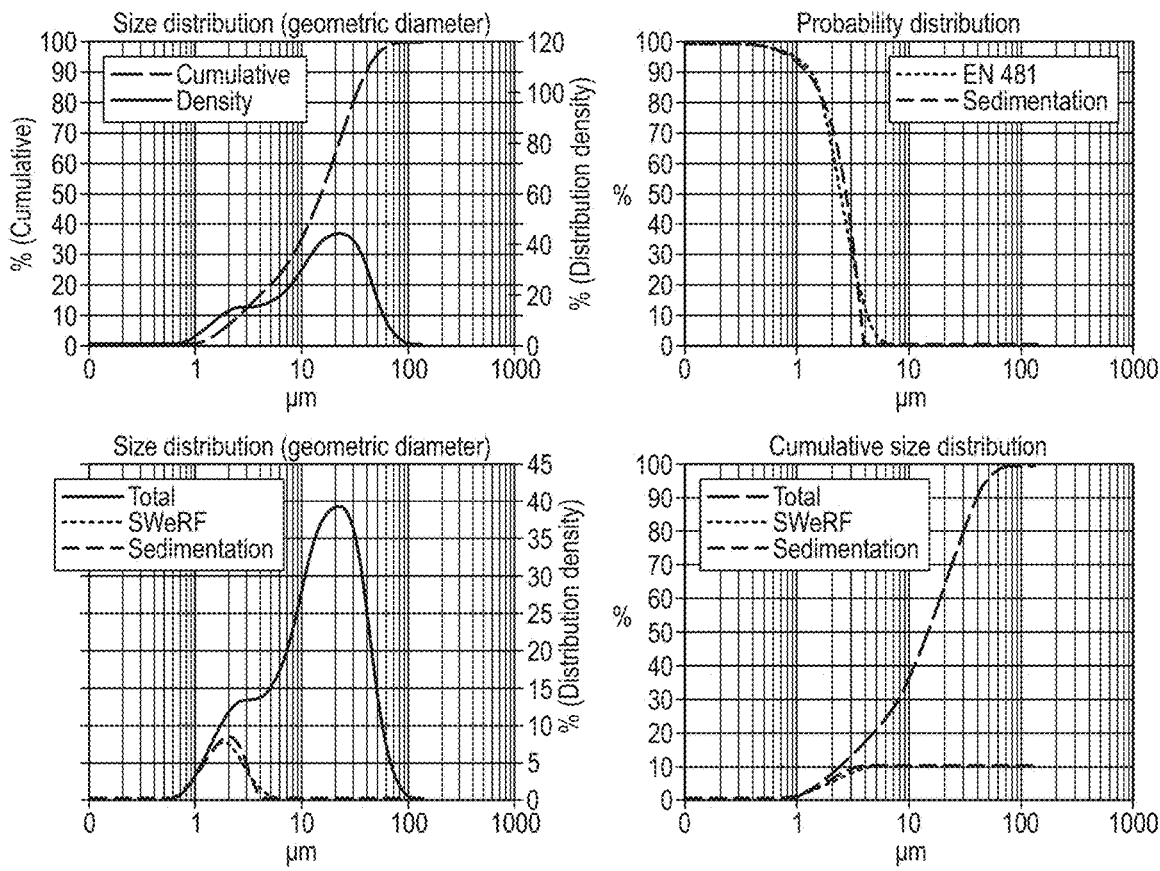
FIG. 12 is a second plot of filler Microwhite 100.
Figure 13:
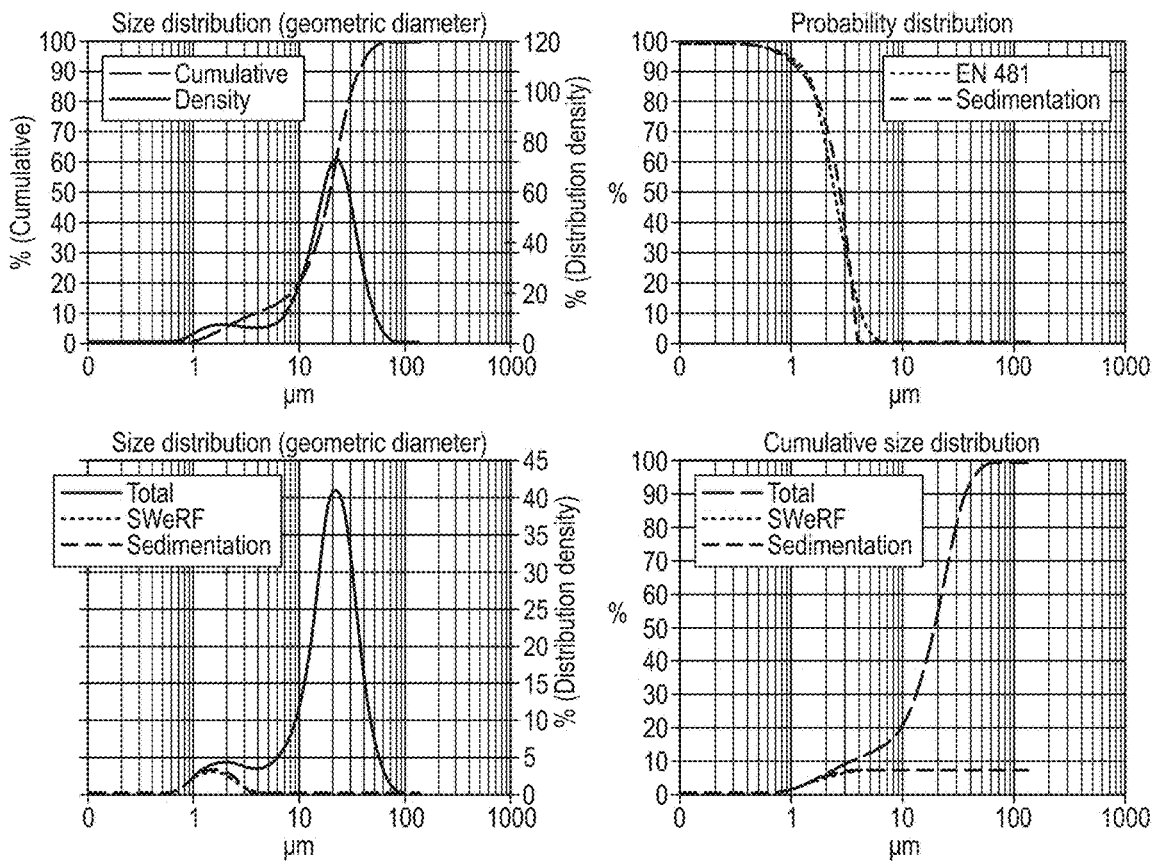
FIG. 13 is a second plot of filler Pulpro-20.
Figure 14:
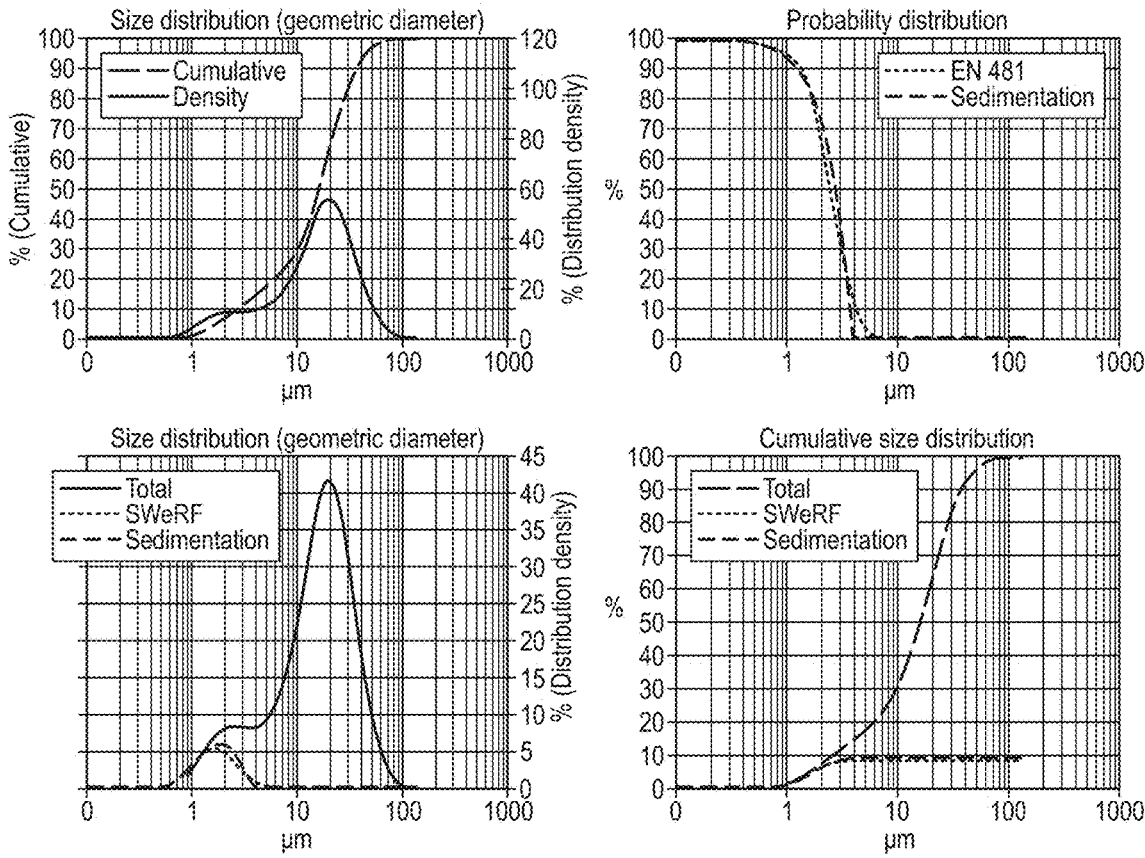
FIG. 14 is a plot of filler Snowhite 21.
Figure 15:
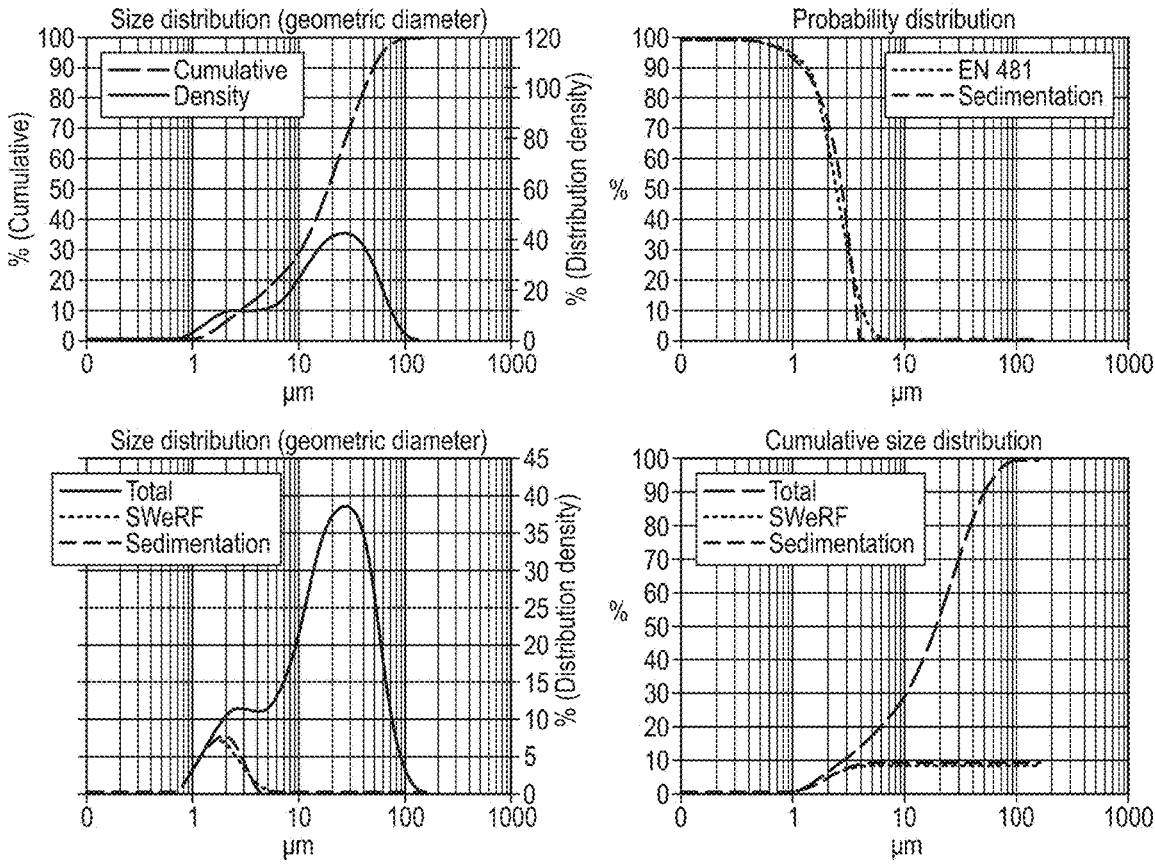
FIG. 15 is a plot of filler S-200.
Figure 16:
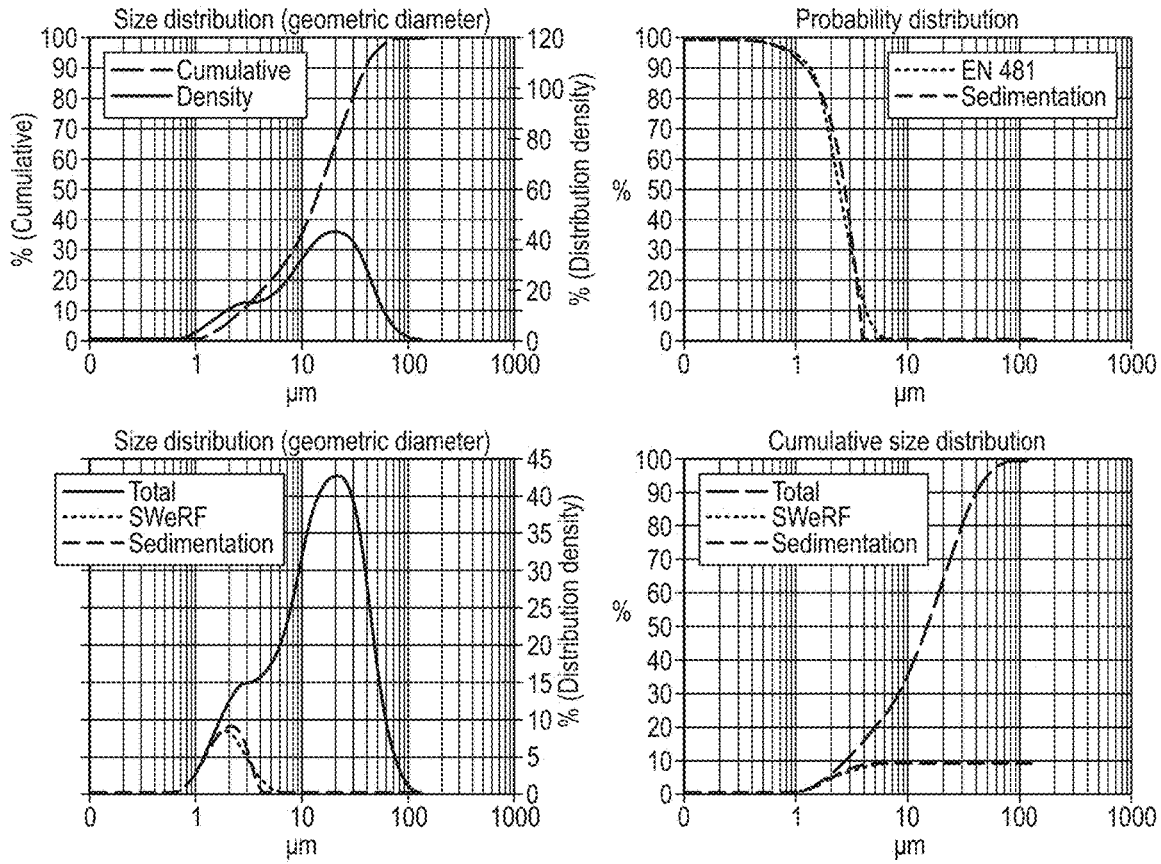
FIG. 16 is a plot of filler Marblehill.
Figure 17:
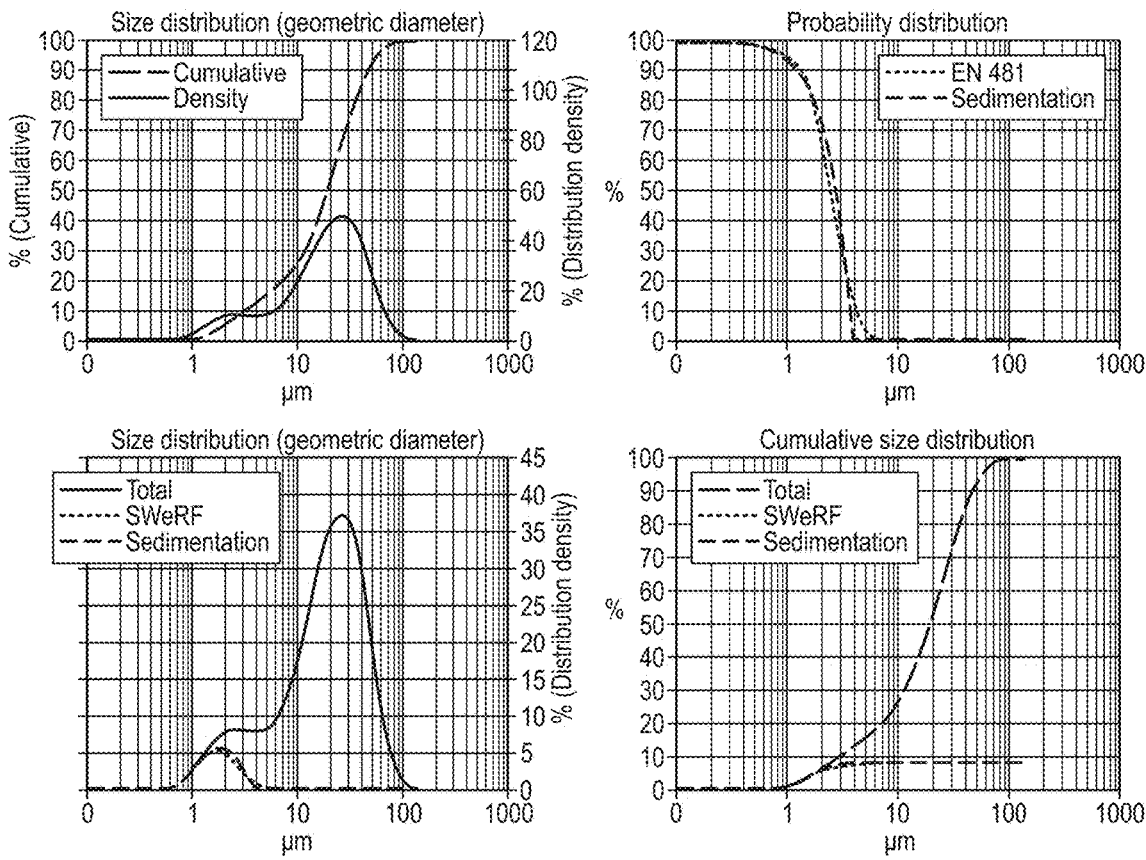
FIG. 17 is a plot of filler G260 RM 71778.

The XRD experiment on gypsum spiked with 0.5% and 0.1% quartz shows excellent initial sensitivity, as shown in FIGS. 5 and 6. Even though this only is three calibration points (FIG. 7), a scan of selenite indicates the material is 0.056% quartz (FIG. 8).

Various carbonates which can be used as a filler were tested for SWeRF and SWeRFcs by the method described above. These values are provided in Table 2 below. See also FIGS. 9-17 for supporting plots.

TABLE 2

Estimated Respirable Fractions

|  | SWeRF = | SWeRFcs = |
|---|---|---|
| 2016-148 #1 80388-CP Filler | 7.34 | 0.09 |
| 2016-148 #2 Marblewhite 310 | 8.30 | 0.030 |
| 2016-148 #3 70283-BP-U | 7.02 | 0.052 |
| 2016-159 #1 62303-Microwhite 100 Sylacauga | 9.63 | 0.12 |
| 2016-159 #2 66342-Pulpro-20 | 6.69 | 0.37 |
| 2016-159 #3 63305-Snowhite 21 | 8.73 | 0.33 |
| 2016-159 #4 70999 S-200 | 8.21 | 0.020 |
| 2016-159 #5 60208 Microwhite 100 Marblehill | 9.07 | 0.027 |
| 2016-182 #1 G260 RM 71778 | 7.75 | 0.024 |

Table 3 lists the particle size distribution for the carbonates.

FIGS. 9-17 provide plots supporting the data in Table 3. The data in Table 3 indicate that 5 carbonates out of all carbonates listed in Table 2 meet the new silica limit. A person of skill will also readily understand that the final contribution to the product of the respirable fraction depends on the formulation level.

Further embodiments provide a method in which particles are analyzed individually to measure concentrations of respirable particles (such as for example, silica, silicate minerals, asbestos, and any other particles that may be hazardous to a human if inhaled) in a bulk material for safety assessment.

In this method, a sample of bulk material is dispersed and resuspended in a suitable medium. The sample can be resuspended in water or in an organic solvent, including, but not limited to, isopropanol or ethanol. The choice of a medium depends on the water solubility for a particular material to be analyzed. For materials soluble in water, an organic solvent is used.

TABLE 3

| Omya BP-LU RUN | VOLUME (cc) | DENSITY (g/cc) | SMI Marblewhite 310 RUN | VOLUME (cc) | DENSITY (g/cc) | Imerys CP-Filler RUN | VOLUME (cc) | DENSITY (g/cc) |
|---|---|---|---|---|---|---|---|---|
| 1 | 0.3353 | 2.9871 | 1 | 0.3569 | 2.8116 | 1 | 0.3603 | 2.7781 |
| 2 | 0.3332 | 3.0063 | 2 | 0.4005 | 2.5052 | 2 | 0.3588 | 2.7903 |
| 3 | 0.3366 | 2.9757 | 3 | 0.3612 | 2.7779 | 3 | 0.3603 | 2.7789 |
| 4 | 0.3354 | 2.9858 | 4 | 0.3621 | 2.7711 | 4 | 0.3639 | 2.7507 |
| 5 | 0.3392 | 2.9528 | 5 | 0.3642 | 2.7551 | 5 | 0.3667 | 2.7299 |
| 6 | 0.3384 | 2.9596 | 6 | 0.3646 | 2.7523 | 6 | 0.3689 | 2.7135 |
| 7 | 0.3397 | 2.9485 | 7 | 0.3659 | 2.7420 | 7 | 0.3707 | 2.7005 |
| 8 | 0.3391 | 2.9534 | 8 | 0.3257 | 3.0811 | 8 | 0.3727 | 0.6863 |
| 9 | 0.3413 | 2.9347 | 9 | 0.3703 | 2.7096 | 9 | 0.3745 | 2.6734 |
| 10 | 0.3405 | 2.9414 | 10 | 0.3700 | 2.7121 | 10 | 0.3722 | 2.6894 |
| average | 0.3379 | 2.9645 | average | 0.3641 | 2.7618 | average | 0.3669 | 2.7291 |
| std. dev. | 0.0026 | 0.0231 | std. dev. | 0.0181 | 0.1400 | std. dev. | 0.0058 | 0.0430 |

| Imerys Microwhite 100-Sylacauga RUN | VOLUME (cc) | DENSITY (g/cc) | Imerys Microwhite 100-Marblehill RUN | VOLUME (cc) | DENSITY (g/cc) | Huber G260 RUN | VOLUME (cc) | DENSITY (g/cc) |
|---|---|---|---|---|---|---|---|---|
| 1 | 0.3666 | 2.7324 | 1 | 0.3694 | 2.7272 | 1 | 0.3683 | 2.7211 |
| 2 | 0.3670 | 2.7295 | 2 | 0.3711 | 2.7141 | 2 | 0.3689 | 2.7172 |
| 3 | 0.3700 | 2.7073 | 3 | 0.3741 | 2.6927 | 3 | 0.3691 | 2.7159 |
| 4 | 0.3702 | 2.7058 | 4 | 0.3768 | 2.6735 | 4 | 0.3699 | 2.7098 |
| 5 | 0.3705 | 2.7042 | 5 | 0.3789 | 2.6587 | 5 | 0.3688 | 2.7174 |
| 6 | 0.3731 | 2.6853 | 6 | 0.3804 | 2.6483 | 6 | 0.3714 | 2.6985 |
| 7 | 0.3731 | 2.6849 | 7 | 0.3822 | 2.6354 | 7 | 0.3682 | 2.7220 |
| 8 | 0.3742 | 2.6775 | 8 | 0.3815 | 2.6406 | 8 | 0.3709 | 2.7026 |
| 9 | 0.3729 | 2.6864 | 9 | 0.3820 | 2.6370 | 9 | 0.3675 | 2.7274 |
| 10 | 0.3744 | 2.6759 | 10 | 0.3789 | 2.6582 | 10 | 0.3683 | 2.7215 |
| average | 0.3712 | 2.6989 | average | 0.3775 | 2.6686 | average | 0.3691 | 2.7153 |
| std. dev. | 0.0028 | 0.0204 | std. dev. | 0.0046 | 0.0327 | std. dev. | 0.0012 | 0.0091 |

| JaJack S-200 RUN | VOLUME (cc) | DENSITY (g/cc) | Omya Snowhite 21 RUN | VOLUME (cc) | DENSITY (g/cc) | Omya Pulpro 20 RUN | VOLUME (cc) | DENSITY (g/cc) |
|---|---|---|---|---|---|---|---|---|
| 1 | 0.3581 | 2.7958 | 1 | 0.3615 | 2.8165 | 1 | 0.3596 | 2.8497 |
| 2 | 0.3572 | 2.8031 | 2 | 0.3609 | 2.8212 | 2 | 0.3555 | 2.8826 |
| 3 | 0.3595 | 2.7851 | 3 | 0.3643 | 2.7949 | 3 | 0.3583 | 2.8598 |
| 4 | 0.3594 | 2.7854 | 4 | 0.3647 | 2.7913 | 4 | 0.3713 | 2.7598 |
| 5 | 0.3631 | 2.7573 | 5 | 0.3676 | 2.7693 | 5 | 0.3574 | 2.8677 |
| 6 | 0.3618 | 2.7672 | 6 | 0.3680 | 2.7663 | 6 | 0.3593 | 2.8518 |
| 7 | 0.3607 | 2.7758 | 7 | 0.3701 | 2.7512 | 7 | 0.3594 | 2.8513 |
| 8 | 0.3597 | 2.7831 | 8 | 0.3701 | 2.7508 | 8 | 0.3649 | 2.8083 |
| 9 | 0.3630 | 2.7583 | 9 | 0.3694 | 2.7562 | 9 | 0.3597 | 2.8487 |
| 10 | 0.3619 | 2.7668 | 10 | 0.3714 | 2.7415 | 10 | 0.3619 | 2.8320 |
| average | 0.3604 | 2.7778 | average | 0.3668 | 2.7759 | average | 0.3607 | 2.8412 |
| std. dev. | 0.0020 | 0.0154 | std. dev. | 0.0037 | 0.0284 | std. dev. | 0.0045 | 0.0348 |

A bulk material suspended in a medium can be subjected to filtration through a membrane filter with pore sizes suitable for retaining particles in the respirable size range. The respirable size range can be less than 20 μm in some applications, whereas in other applications, it can be less than 10 μm. This method can be performed with 0.4-μm pore-sized polycarbonate filter to ensure all particles in the respirable size range are captured.

In one application of the present method, particles retained on the membrane filter by filtration are air-dried and coated with a thin layer of carbon before being subjected to analysis.

In the present method, an analysis of respirable particles is conducted by a scanning electron microscope (abbreviated as SEM) interfaced with an energy dispersive X-ray spectrometer (abbreviated as EDS). In this analysis, individual particles in a sample are analyzed for two different properties:

a) morphological characteristics, including the particle's size and shape; and b) chemical (elemental) composition.

One suitable instrumental setup for the present method includes a computer-controlled scanning electron microscope (SEM) interfaced with an energy dispersive X-ray spectrometer (EDS). This technique can be used to obtain accurate morphological (size, shape, etc.) and (elemental) compositional characterizations of thousands of individual particles.

Morphology filters can be used to select a subset of detected particles for further EDS compositional analyses—only particles in the respirable size range (e.g., <10 μm) can be selected if needed. This allows an adequate sampling and counting of deposited particles on the filter in a time-efficient manner.

Results of this analysis are shown in FIGS. 18□20. FIG. 18 depicts a fraction of the filter area imaged by SEM and converted to a binary image, in which particles of interest (bright feature in the left frame) are identified for further EDS analysis (right frame).

FIG. 19 provides the EDS composition analysis of particles marked in FIG. 18. The results from particle sizing are tabulated below the field image in FIG. 19.

FIG. 20 is an example of the EDS X-ray spectrum acquired for one particle (most likely dolomite) identified in FIG. 18. The results from the EDS analysis are tabulated below the spectrum in FIG. 20.

In the present method, a large number of particles can be accurately analyzed for each particle's morphology and chemical composition. The present method creates a multi-dimensional raw dataset (or a profile) of the particles for the sample. In this method, each particle is characterized by its morphological parameters (such as shape and size) and chemical composition.

In one application of the present method, a sample comprising 10% (by weight) respirable silica mixed in gypsum is analyzed for morphology and chemical composition of individual particles. A profile for this sample is shown in Table 4 below. As can be seen from Table 4, the raw dataset may include the following morphological characteristics of a particle: the area, aspect ratio, volume and diameter. In addition, the particle's chemical characteristics are represented by its elemental composition. This is particularly important for identifying different particle types (e.g., gypsum, quartz, calcium carbonate). In this example, each particle was analyzed for the presence of calcium (Ca), sulfur (S) and silicon (Si).

TABLE 4

Selected output parameters from a computer-controlled SEM-EDS analysis, for a sample made with known quantities of gypsum and respirable silica mixed together.

| Particle ID | Area ($\mu m^2$) | Aspect Ratio[a] | Volume ($\mu m^3$)[b] Sphere | Prolate Spheroid | Area Equivalent Diameter (μm) | Relative Elemental X-ray Intensity[c] Ca % | S % | Si % |
|---|---|---|---|---|---|---|---|---|
| P4939 | 2.60 | 1.63 | 9.93 | 2.09 | 1.82 | 28.59 | 25.13 | 46.28 |
| P4940 | 0.23 | 1.74 | 0.26 | 0.05 | 0.54 | 5.51 | 6.09 | 88.40 |
| P4969 | 1.33 | 1.82 | 3.64 | 0.76 | 1.30 | 11.06 | 11.18 | 77.76 |
| P4973 | 3.20 | 1.56 | 13.54 | 2.72 | 2.02 | 24.57 | 21.71 | 53.72 |
| P4975 | 2.01 | 1.40 | 6.71 | 1.70 | 1.60 | 44.10 | 43.48 | 12.42 |
| P4979 | 0.17 | 1.52 | 0.16 | 0.03 | 0.46 | 37.26 | 42.31 | 20.43 |
| P4990 | 0.15 | 1.35 | 0.13 | 0.03 | 0.43 | 20.18 | 17.71 | 62.11 |
| P4998 | 0.45 | 1.17 | 0.72 | 0.19 | 0.76 | 44.35 | 44.08 | 11.57 |
| P5008 | 0.30 | 1.42 | 0.40 | 0.09 | 0.62 | 9.42 | 7.65 | 82.93 |
| P5011 | 0.43 | 1.86 | 0.67 | 0.14 | 0.74 | 15.32 | 15.67 | 69.02 |
| P5020 | 1.11 | 1.48 | 2.77 | 0.65 | 1.19 | 6.84 | 5.40 | 87.76 |
| P5024 | 8.51 | 1.41 | 58.72 | 11.18 | 3.29 | 11.26 | 10.60 | 78.14 |
| P5025 | 0.18 | 1.23 | 0.18 | 0.04 | 0.48 | 14.14 | 14.23 | 71.63 |
| P5031 | 0.37 | 1.85 | 0.53 | 0.10 | 0.68 | 18.05 | 18.92 | 63.03 |
| P5036 | 0.36 | 1.28 | 0.50 | 0.12 | 0.67 | 32.83 | 30.99 | 36.18 |
| P5043 | 0.30 | 1.84 | 0.40 | 0.08 | 0.62 | 13.98 | 15.15 | 70.87 |
| P5047 | 0.14 | 1.46 | 0.12 | 0.03 | 0.42 | 17.67 | 16.55 | 65.78 |
| P5058 | 0.20 | 1.68 | 0.21 | 0.05 | 0.50 | 42.49 | 42.56 | 14.95 |
| P5073 | 0.16 | 1.58 | 0.15 | 0.03 | 0.45 | 12.31 | 10.66 | 77.03 |
| P5076 | 0.49 | 1.75 | 0.82 | 0.15 | 0.79 | 9.93 | 10.71 | 79.36 |
| P5090 | 10.24 | 1.95 | 77.40 | 15.98 | 3.61 | 47.22 | 41.82 | 10.95 |

[a]Aspect ratio = length/width, dimensionless; a measure of sphericity of a particle-1 for spheres, >1 for irregular particles.
[b]Particle volumes estimated for two different shapes (later to be used for mass approximation with density values for different composition.
[c]Only relevant elements are shown; due to the use of polycarbonate filter membrane for sample preparation, oxygen (O) was not included in semi-quantification, and gypsum was represented by the elemental presence of Ca and S. Silica was represented by Si.

The large amount of information obtained for morphology and chemical makeup of particles affords a plethora of ways in which the raw data can be analyzed. The following example (FIG. 21) presents the frequency distribution of sizes (as area equivalent diameter, AED) of particles with values of Si X-ray relative intensity >5%, for the same sample as in Table 4. Another way to present these data is to show the Si contents in particles as a function of particle size (FIG. 22).

The present method may also include a step of further characterizing and grouping particles according to a combination of particle characteristics listed (but not limited to) in Table 4. For example, normalized X-ray counts (net counts divided by particle size) can be used to differentiate crystalline and amorphous $SiO_2$.

Additional data analyses can be conducted with a specifically complied code program to selectively group particles according to their characteristics, including shape, size, chemical composition and any combinations of parameters from the raw dataset.

The invention will be now described in more detail by the following non-limiting Examples.

Example 1

A small amount of weighed bulk material was well-mixed and suspended in known volume (50-100 ml) of deionized water or isopropanol depending on the water solubility of the material. An aliquot (generally <10 ml) was pressure filtered through 25-mm diameter, 0.4-μm pore-sized polycarbonate filter. Particles deposited on the membrane filter were air-dried and coated with a thin layer of carbon before being subject to instrument analysis.

Figure 18:
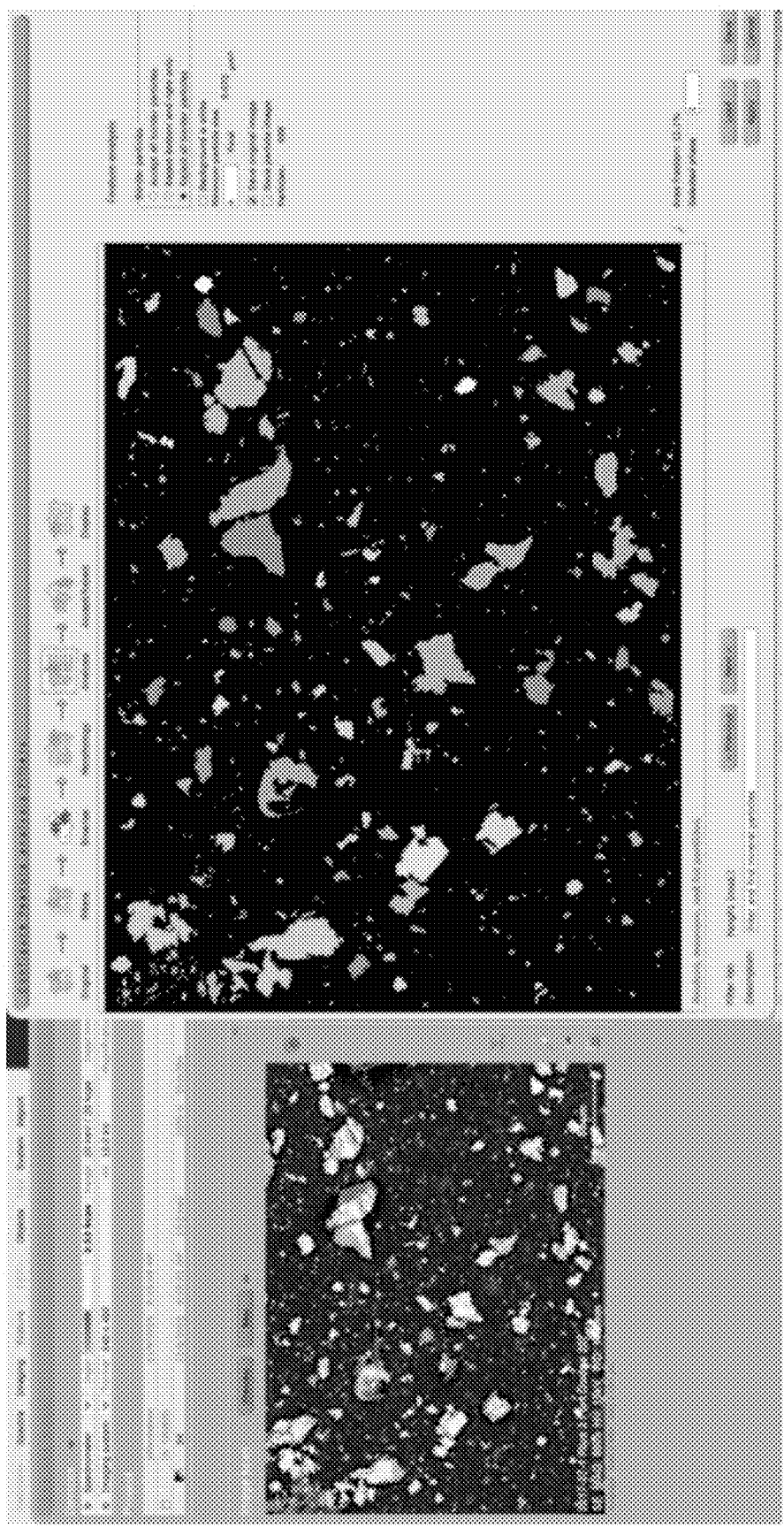
FIG. 18 is an example of ESPRIT's Feature analysis workspace: a fraction of the filter area is imaged by SEM and converted to binary image, in which particles of interest (bright feature in the left frame) are identified for further EDS analysis (right frame).
Figure 19:
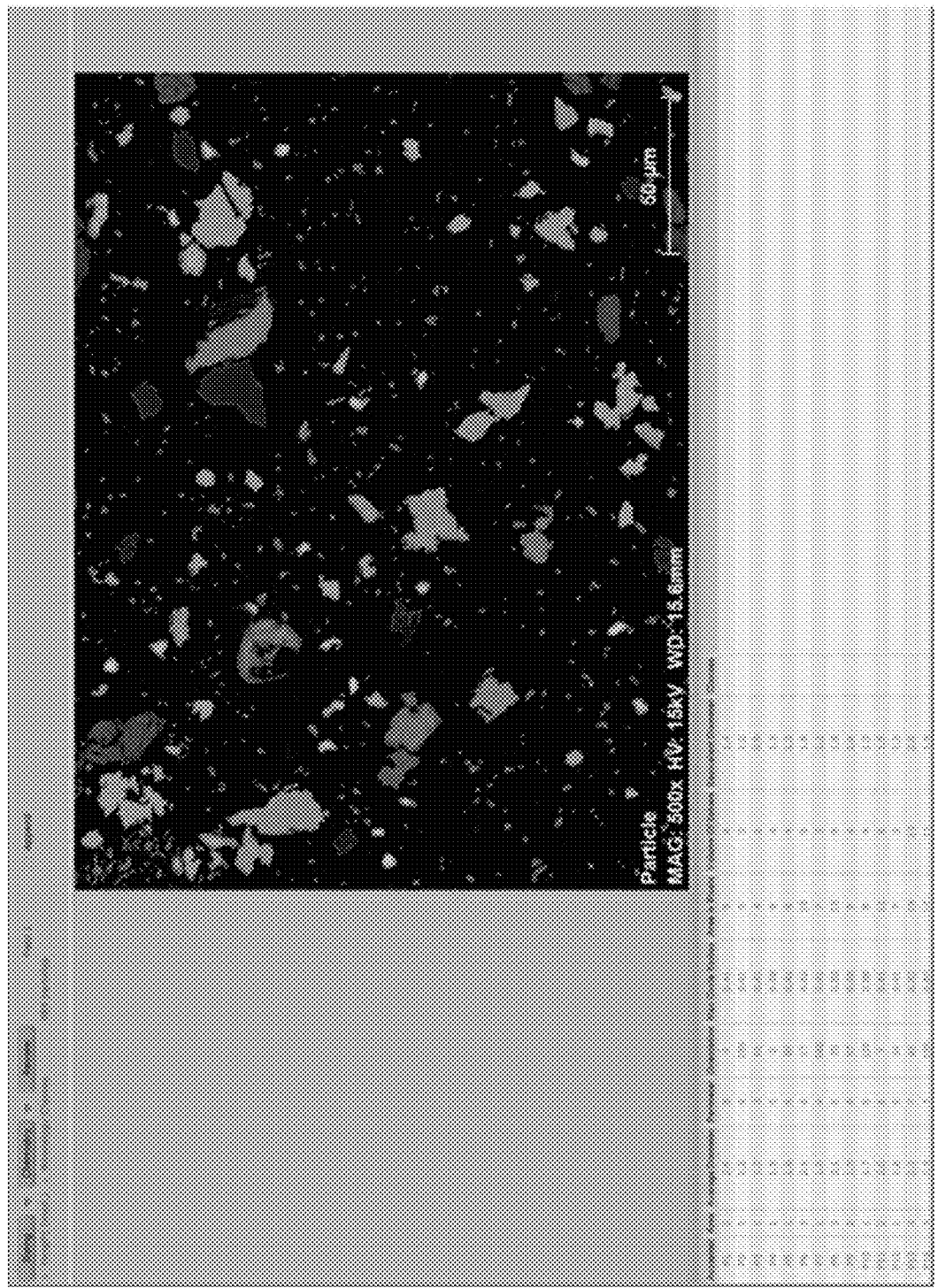
FIG. 19 is an example of automated particle analysis workspace: EDS composition analyses of particles marked in FIG. 18 are in progress; note that results from particle sizing are tabulated below the field image.
Figure 20:
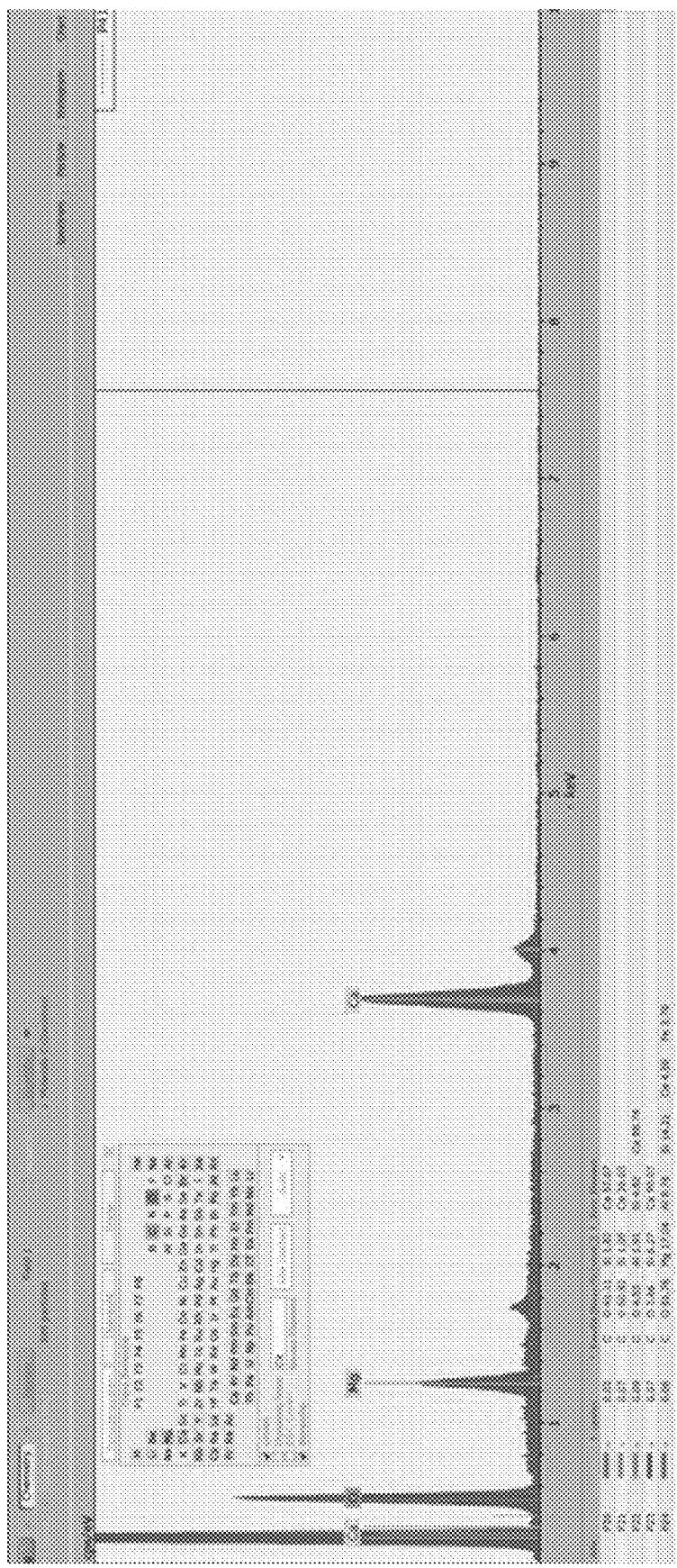
FIG. 20 is the particle analysis workspace: an example EDS X-ray spectrum acquired for one particle (most likely dolomite) identified in FIG. 18; note that results from EDS are tabulated below the spectrum.

An automated, computer-controlled particle analysis was conducted by a scanning electron microscope (SEM) interfaced with an energy dispersive X-ray spectrometer (EDS). The automated particle analysis was used to provide morphological (size, shape, etc.) and (elemental) compositional characterizations of individual particles, results of which are shown in FIGS. 18-20. Morphology filters were used to select a subset of detected particles for further EDS compositional analyses. In this example, only particles in the respirable size range (<10 μm) were selected.

Example 2

A sample comprising 10% (mass concentration) respirable silica mixed in gypsum (micronizing mill was used to homogenize the mixture) was prepared. 8.4 mg of the mixture was suspended in 50 ml isopropanol; and 3 ml of the suspension was filtered through 25-mm diameter, 0.4-μm pore-sized polycarbonate filter, resulting in 0.504 mg of material retained on a deposition area of 3.14 $cm^2$.

Figure 21:
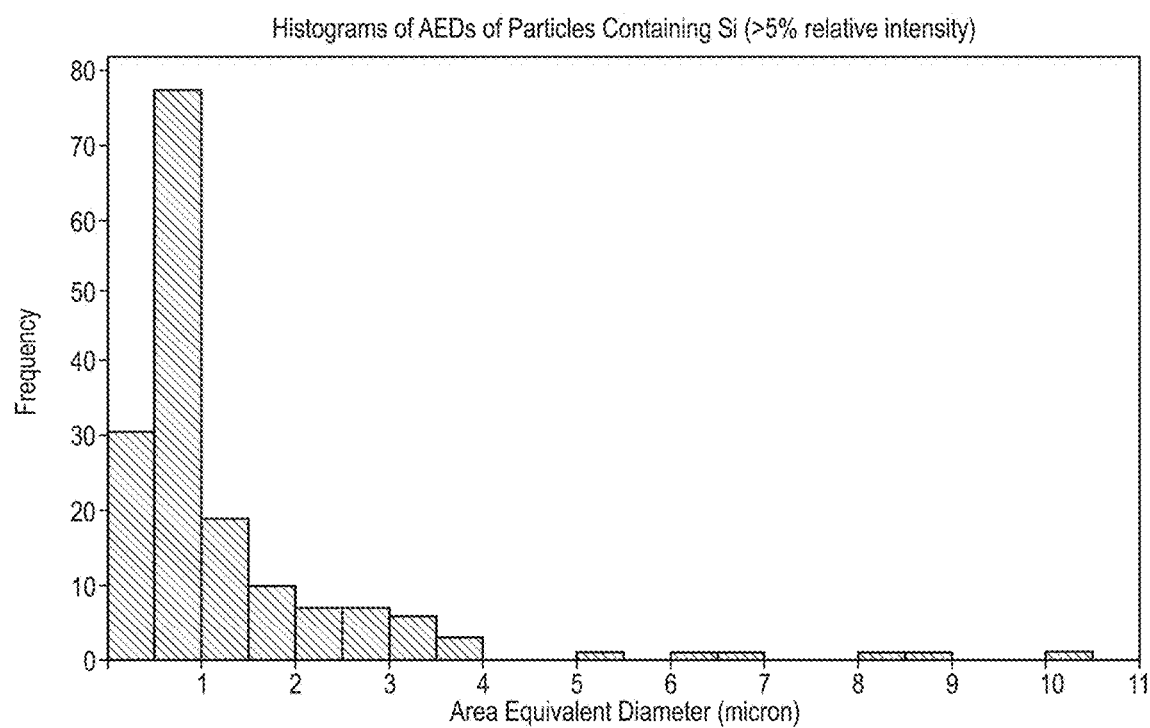
FIG. 21 is a histogram of size (as AED) frequency of particles with Si relative intensity >5% (cf. Table 4).
Figure 22:
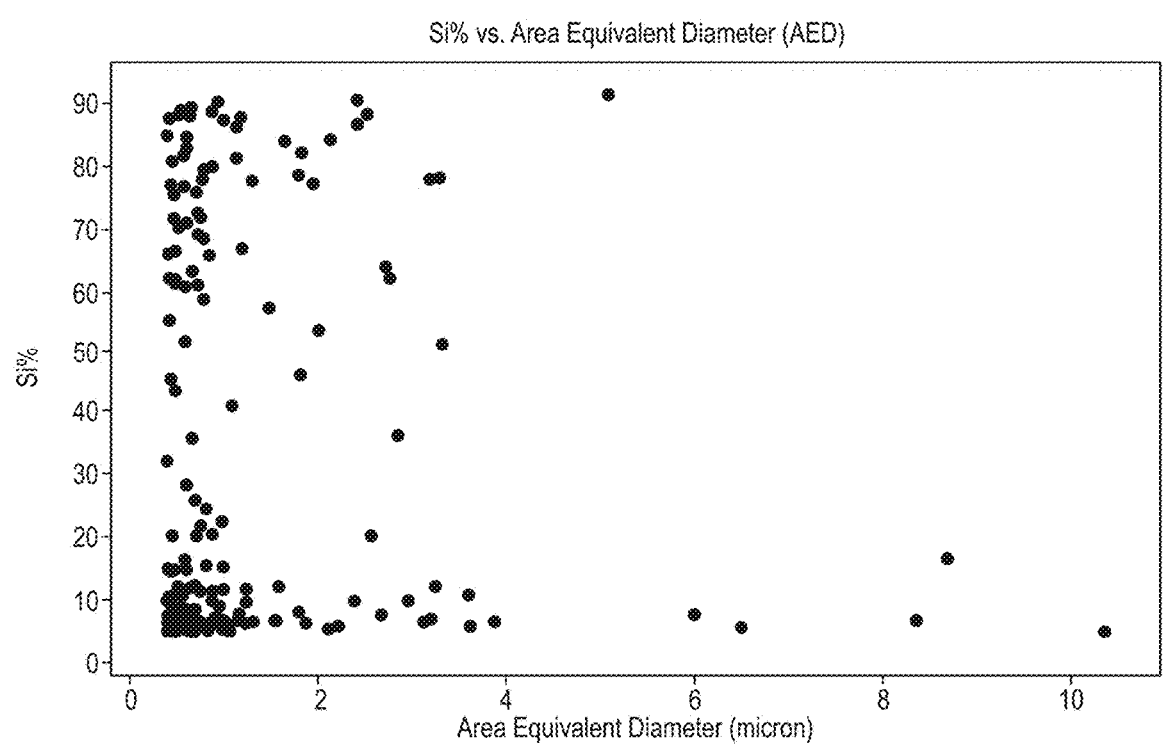
FIG. 22 reports Si contents in particles (with relative intensity >%5) as a function of size.

The sample was analyzed as described in Example 1 and the particle analysis data was tabulated in Table 4 and were also presented in FIGS. 21 and 22.

In this analysis, particles containing ≥10%, Si (relative intensity) and ≤10 μm were included in the calculation as respirable silica, and density value of 2.65 $g/cm^3$ was used to estimate a particle mass, assuming a prolate spheroid particle shape. Knowing the fraction of the deposition area analyzed by SEM-EDS, the mass concentration of respirable silica determined by the analysis was 9.8%, which is consistent with that of the prepared sample mixture.

What is claimed is:

1. A method for detecting respirable particles in a bulk material sample comprising particles, the method comprising:
    weighing the bulk material sample;
    resuspending the particles of the bulk material sample in a medium selected from water and/or organic solvent, and filtering the suspension through a filter with a nominal pore size sufficiently small to retain the particles in the respirable size range;
    analyzing morphology of the particles;
    analyzing chemical composition of the particles;
    creating a profile of the particles, wherein each particle in the profile is characterized by its shape, size and chemical composition;
    counting the particles as a total number of the particles in the bulk material sample;
    selecting particles from the profile which match the size smaller than 20 microns and chemical composition of a respirable particle comprising silica ($SiO_2$);
    counting the selected particles as respirable particles; and
    calculating a percentage of the respirable particles from the total number of the particles in the bulk material sample.

2. The method of claim 1, wherein the morphology and chemical composition of the particles are analyzed by a scanning electron microscope interfaced with an energy dispersive X-ray spectrometer.

3. The method of claim 1, wherein the particles are retained on a filter, and wherein the morphology and chemical composition of the particles are analyzed by a scanning electron microscope interfaced with an energy dispersive X-ray spectrometer.

4. The method of claim 1, wherein the bulk material is a mixture of inorganic compounds.

5. The method of claim 1, wherein the respirable particles are smaller than 10 microns.

6. The method of claim 1, wherein the bulk material is selected from the group consisting of gypsum and calcium carbonate.

7. The method of claim 1, wherein the filter is a polycarbonate filter.

* * * * *